(12) United States Patent
Batista et al.

(10) Patent No.: US 8,657,943 B2
(45) Date of Patent: Feb. 25, 2014

(54) 1-HYDROXY-2-O-ACYL-SN-GLYCERO-3-PHOSPHOCHOLINE COMPOUNDS, PREPARATION PROCESS, ANTIFOULING COMPOSITION, PROCESS FOR ITS PREPARATION, METHOD TO PREVENT FOULING, METHOD TO TURN A SURFACE INTO AN ANTIFOULING SURFACE, AND, COVERED SURFACE

(75) Inventors: William Romao Batista, Arraial do Cabo (BR); Ricardo Coutinho, Arraial do Cabo (BR); Maria Campos Beta Neves, Arraial do Cabo (BR); Claudio Cerqueira Lopes, Rio de Janeiro (BR); Rosangela Sabbatini Lopes, Rio de Janeiro (BR); Vanessa de Almeida Martins, Rio de Janeiro (BR); Renato Crespo Pereira, Niteroi (BR)

(73) Assignee: UFRJ, IEAPM, UFF, Rio de Janeiro (BR)

( * ) Notice: Subject to any disclaimer, the term of this patent is extended or adjusted under 35 U.S.C. 154(b) by 173 days.

(21) Appl. No.: 13/307,598

(22) Filed: Nov. 30, 2011

(65) Prior Publication Data
US 2012/0135134 A1 May 31, 2012

(30) Foreign Application Priority Data

Nov. 30, 2010 (BR) .................................. 1004585
Nov. 30, 2010 (BR) .................................. 1004858-8

(51) Int. Cl.
C09D 5/16 (2006.01)
A01N 57/10 (2006.01)
A01N 57/12 (2006.01)

(52) U.S. Cl.
USPC ................. 106/18.31; 106/15.05; 424/78.09; 514/75; 514/79; 523/122; 523/177

(58) Field of Classification Search
USPC ............ 106/15.05, 18.31; 424/78.09; 514/75, 514/78; 523/122, 177
See application file for complete search history.

(56) References Cited

U.S. PATENT DOCUMENTS

| 5,306,840 A * | 4/1994 | Tronconi ...................... 558/146 |
| 5,827,836 A * | 10/1998 | Peterson et al. ................ 514/77 |
| 6,583,251 B1 * | 6/2003 | Chaikof et al. ............... 526/277 |
| 2008/0171191 A1 * | 7/2008 | Reppy et al. ............... 428/315.7 |

FOREIGN PATENT DOCUMENTS

JP        2007-119643 A  *  5/2007

OTHER PUBLICATIONS

Derwent Accession Number: 2009:1231143 (abstract of WO 2009123191 A1) Oct. 2009.*
Derwent Accession Number: 2008:857475 (abstract of US 20080171191 A1) Jul. 2008.*
Derwent Accession Number: 2007:531837 (abstract of Japanese Patent Specification No. JP 2007119643A) May 2007.*
Derwent Accession Number: 2003:485729 (abstract of US Patent No. 6,583,251) Jun. 2003.*
Derwent Accession Number: 1999:359734 (abstract of WO 9927364) Jun. 1999.*
Derwent Accession Number: 1998:705959 (abstract of US 582836 A1) Oct. 1998.*
Derwent-Accession Number: 2010-A51546 (abstract of Chinese Patent Specification No. Cn 101605911A) Dec. 2009.*

* cited by examiner

*Primary Examiner* — Anthony J Green
(74) *Attorney, Agent, or Firm* — Laurence P. Colton; Smith Risley Tempel Santos LLC

(57) ABSTRACT

1-OH-2-acyl-sn-glycero-3-phosphocholine compounds and its analogs, pure or mixed, having formula WCH2CHXCH2PO3YCH2CH2Z, where W is preferably a hydroxyl group or an O-acyl group containing from 2 to 22 carbon atoms, and where X is preferably an O-acyl group containing from 2 to 22 carbon atoms or a hydroxyl (OH) and where Y may be an (O⁻) or OH and where Z is preferably a trimethyl-ammonium group [N⁺(CH₃)₃] can be protonated dimethyl ammonium [N⁺H(CH₃)₂] group. In the O-acyl groups containing 18 carbon atoms can be observed from 0 to 3 instaurations, useful as biocidal agents; processes for their preparation; and antifouling compositions, preferably paints useful in susceptible fouling surfaces, such as hulls of vessels. Methods to turn a surface into an antifouling surface, to a method to prevent fouling and to the antifouling surfaces comprising a coating of the said antifouling composition.

16 Claims, 10 Drawing Sheets

1-HYDROXY-2-O-ACYL-SN-GLYCERO-3-PHOSPHOCHOLINE COMPOUNDS, PREPARATION PROCESS, ANTIFOULING COMPOSITION, PROCESS FOR ITS PREPARATION, METHOD TO PREVENT FOULING, METHOD TO TURN A SURFACE INTO AN ANTIFOULING SURFACE, AND, COVERED SURFACE

STATEMENT OF RELATED APPLICATIONS

This application claims convention priority under 35 USC 119(a) to Brazilian Patent Application No. PI 1004858-8 filed on 30 Nov. 2010 and Brazilian Patent Application No. 020100111690 filed on 30 Nov. 2010.

BACKGROUND OF THE INVENTION

1. Field of the Invention

The present invention relates to novel 1-OH-2-acyl-sn-glycero-3-phosphocholine compounds and its analogs, pure or mixed, having formula $WCH_2CHXCH_2PO_3YCH_2CH_2Z$, where W is preferably a hydroxyl group or an O-acyl group containing from 2 to 22 carbon atoms, and where X is preferably an O-acyl group containing from 2 to 22 carbon atoms or a hydroxyl (OH) and where Y may be an ($O^-$) or OH and where Z is preferably a trimethyl-ammonium group [$N^+$ $(CH_3)_3$] can be protonated dimethyl ammonium [$N^+H$ $(CH_3)_2$] group. In the O-acyl groups containing 18 carbon atoms can be observed from 0 to 3 instaurations, useful as biocidal agents; processes for their preparation; and antifouling compositions, preferably paints useful in susceptible fouling surfaces, such as hulls of vessels.

The present invention is also directed to methods to turn a surface into an antifouling surface, to a method to prevent fouling and to the antifouling surfaces comprising a coating of the said antifouling composition.

The present invention applies to the industrial technical field of coatings and paints for underwater protection, against harmful effects of biofouling, of submerged or floating structures in fresh or salt water, e.g., hulls of vessels, buoys, oil platforms and ducts/pipes. Such product may be added to the coating material by directly dispersion, by forming chemical bonds, incorporated by microencapsulation or combination of these means.

2. Prior Art

The present invention was motivated by the global issue related to the prohibition of use, adopted on 5 Oct. 2001 by the International Maritime Organization (IMO) and promulgated on 17 September 2008, of the compound known as tri-butyl tin (TBT), major and most effective biocide used in marine coatings and antifouling paints (IMO, 2010; GIPPERTH, 2009), and also believing that the use of a biocide/repellent based on natural compounds is indeed the best answer for the replacement of TBT in the fight against marine biofouling.

The present invention is justified by the need for the existence of commercial products with antifouling biocide/repellent action, not environmentally friendly, of easy synthesis, which involves the use of a cheap and abundant raw material associated with a synthetic route easy to perform, which can be used in the preparation of coatings and antifouling marine paints.

Biofouling

Biofouling is a natural process that occurs with any structure placed in contact with water where there is the presence of micro-organisms. It begins immediately after the object was placed in the sea, by the adhesion of organic substances and materials dissolved in water, developing into a situation where there is the presence of marine macro-organisms such as algae, barnacles and mussels (CALLOW and CALLOW, 2006; BHADURY and WRIGHT, 2004; YEBRA et al., 2004).

Problems due to the presence of biofouling are comprehensive, ranging from the clogging of pipes, through the structural impairment of platforms and reaching the harmful action of the performance of vessels by increasing the drag force. From a military standpoint, the growth of fouling on the hulls of vessels is considered a serious and routine problem, due to the fact that decrease the final speed of the vessel and its maneuverability, blocking cooling windows, increase fuel mileage and compel the dockings or more frequent assets, contributing to the potential failure of any military action.

Technically the process of biofouling consists of four stages, not strictly sequential, but interdependent. The first stage begins in the first minutes of contact with the water surface, when occurs the accumulation of organic molecules such as polysaccharides and proteins. This allows, in the coming hours (24-96 h), the development of early colonization by bacteria, e.g. *Pseudomonas, Leptothrix, Rhodopseudomonas, Desulfovibrio, Beggiatoa*, and diatomaceus, e.g. *Navicula* e *Nitszchia*, which together with cyanobacteria, e.g. *Phormidium* and *Oscillatoria*, protozoa and rotifers, which exude different polysaccharides, called exopolysaccharides, which in a complex mixture with nucleic acids, proteins, minerals, nutrients, cellular debris and micro-organisms themselves, form the second stage which is called by biofilm (CALLOW and CALLOW, 2006; BHASKAR and BHOSLE, 2005; ARCE et al., 2004).

The presence of biofilm allows micro-organisms have greater protection from predators, toxins and environmental changes, and allows adequate availability of nutrients, seized of the marine environment, which are dispersed in this biofilm. This designation, biofilm, it must not be understood in the strict sense of the word, because in fact the same is not presented as a continuous or homogeneous layer, or as a foil (film), and its structure, heterogeneous in space and time, changing due to external and internal processes (DONLAN, 2002; COSTERTON, et al. 1994). In fact, its structure has, more often, communities of grouped micro-organisms called clusters, having canalith that permit the passage of water bringing nutrients, oxygen, and therefore other possible compounds such as biocides (DONLAN, 2002; DUNNE, 2002; SUTHERLAND, 2001; DAVEY e O'TOOLE, 2000). The formation of a cluster begins with the contact and adhesion of bacteria to an etched surface, forming a small colony that grows due to the multiplication of micro-organisms and the accumulation of exudates exopolysaccharides, and may acquire formats ranging from the mounds to structures like mushrooms, reaching a state of maturity where it initiates an active process of dispersion that allows the formation of new colonies (STOODLEY, et al. 2004; LASPIDOU, 2003; LOOSDRECHT, et al. 1990). The exopolysaccharides are the main compounds of the dehydrated biofilm, accounting for between 50% and 90% of total organic carbon present in it, but when fully hydrated, the water can reach 97% of its weight. They may vary in their physical and chemical properties, but usually consist of heteropolymerics polysaccharides with molecular weight of the order of kiloDaltons, which, due to the type of monosaccharides based on their training e.g. glucuronic acids, galacturonic, manuranico, etc., are generally anionic, casually neutral and rarely positively charged, having hydrophilic and hydrophobic regions. Although alone they form various types of structures within the biofilm, these polysaccharides can interact with other types of molecules such as proteins and lipids, forming what is known as extracellular polymeric substances (EPS) (BHASKAR and BHOSLE, 2005; PARSEK and FUQUA, 2003; DONLAN, 2002; SUTHERLAND, 2001; DeBEER e KOHL, 2001; ALLISON, 1998).

The third stage is the secondary colonization made by macroalgae spores, larvae of barnacles, fungi, protozoa and other bacteria, which transform the biofilm during the first week in a more complex composition.

The fourth stage involves the settlement, and especially the growth of marine macro-organisms such as molluscs, bryozoans, antozoans, polychaetes, tunicates and crustaceans (FLEMMING et al., 1996; BORENSTEIN, 1994).

The type, the extent and the severity of biofouling depends on the factors such as substrate type, water salinity, ambient light, temperature, pollution and available nutrients. Thus, biofouling tends to be a seasonal phenomenon related to geographical location. In polar regions, with temperatures below 5° C., the action of biofouling is low, in temperate zones (5 to 20° C.), the risk is medium, while in tropical and subtropical zones, where temperatures are greater than 20° C., the risk associated with biofouling is high, mainly due to the suitable condition for multiplication of fouling organisms, which is estimated there are over 4000 species with potential to colonize submerged surfaces (PROPELLER, 2004).

Thus, ships that travel or remain in tropical or subtropical areas are subject to more severe attacks by biofouling, particularly in shallow or coastal waters, where there is a greater availability of light, heat and nutrients, e.g. Guanabara Bay, R J.

Control of Biofouling on Ships

The search for products that work effectively as a biocide in vessel paint, dates from the early era of navigation. The man of the sea, has been suffering incessantly the martyrdom of biofouling, and used to laborer scrape for cleaning the hull fouling as the primary palliative.

Two thousand years ago, the wooden hulls of ships were partially covered with lead and painted with mixture of oils infused with of sulfur and arsenic. In 1625, a lethal combination of arsenic, copper and iron powders was considered an important value enough to receive, in England, a patent as an antifouling compound (ANDERSON et al., 2003; PROPELLER, 2002; CLARE, 1995).

Until the first half of the eighteenth century, the most widely used method of combating biofouling of ships remained the drainage or regular scraping to manual docking of living work, a procedure that required tremendous manpower, besides the risk of property damage and lost profits.

There is the record that in 1758, the British frigate HMS Alarm, it was her hull covered with pieces of sheet copper, and that this experiment was considered a success at the time, this procedure by encouraging other ships (CALLOW, 1990).

After the introduction of iron-hulled vessels, the use of copper sheets has been largely discontinued due to problems related to galvanic corrosion, which was virtually ignored at the time. As the main result of this new engineering, has emerged a renewed interest of biocides that could be added to the paints used in painting the hulls of iron.

This perspective has unleashed a flood of products and patents for antifouling compounds, when, in England alone, more than 300 patents have been produced in the late nineteenth century.

In 1860 James McInness used copper sulfate as an antifouling. In 1863 James Tarr and Augustus Wonson were receiving a US patent for an antifouling paint that used copper oxide mixed with coal tar naphtha and benzene.

In 1906, the American Navy tested various antifouling paints in the shipyard in Norfolk, Va. As early as 1908 began the production of paints to painting of vivid works of American ships.

Until 1926, some versions of paint were based in mercuric oxide suspended in various resins and solvents. In this same period, the American Navy replaced the paints based on tar, for resin formulations with more fluid consistency of varnish. This came to facilitate the application of the coating as it does not require heating to fluidize the mixture.

In 1940 major changes in paint technology have resulted in a wide range of chemicals products and the introduction of new formulations of surfaces preparations. But the useful life of conventional antifouling paint was still limited because of ignorance of how to control the release of the biocide contained in them.

After the $2^{nd}$ World War, the emergence of new synthetic resins derived of petroleum, provided paints that has best mechanical properties, which greatly facilitated its implementation. During this time the appearance of organic-tin compounds improved the performance of antifouling paints, so it seemed to have the final answer to such problems (YEBRA et al., 2004).

In 1950 the first record on the broad spectrum of antifouling paints with TBT was made by Van Kerk et al. In the early sixties the excellent property of TBT as antifouling was discovered, making this commercial (YEBRA et al., 2004). While in the seventies many of the antifouling paints were based on the use of copper, the life of these schemes still hovered around 24 months, due to uncontrolled release of biocide used, which increased the cost of repainting and dockings.

The TBT used initially as an adjunct in compound preparations of paints, would become the owner shortly after the lead role, since the development of paint schemes called self-polishing was in progress, and a British patent based upon the composition of TBT with self-polishing copolymer resins obtained by Alexander Milne and George Hails in 1974, revolutionized the industry of the antifouling paints (MILNE and HAILS, 1974). This product has shown excellent control of biofouling and extended the period between dockings. In this combination, the TBT is attached to the polymer-based acrylic through ester links, which are readily hydrolyzed in the slightly alkaline seawater solution (pH ~8.2), releasing the TBT, which can then act as a biocide. The remaining part of the acid copolymer is solubilized by sea water and then exposes a new layer of TBT-copolymer. This particularity allows to effectively control the release rate of biocide, making its action depending on the paint scheme adopted, can last for up to 5 years (PROPELLER, 1998).

However, in the late seventies, oysters that grew close to ports and marines in the Bay d'Arcachon, France, showed a high incidence of malformation in the shell, which affected their marketing and survival (LEWIS, 2002).

In parallel to advancing the use of TBT, several studies related to its possible environmental damage were performed.

In 1982, Alzieu and colleagues performed experiments keeping oysters in tanks of 150 liters which were successively filled and emptied according to the tide, which contained panels painted in a face with TBT fluoride, at concentrations from 0.2 to 2 µg/L. They found that 30% of oysters died after 110 days of exposure and all died at the end of 170 days (WHO, 1990).

It was estimated that concentrations of up to 100 ng/L of TBT in seawater, it causes significant reductions in the growth of mussels (SALAZAR e SALAZAR, 1996).

Abnormalities of reproductive oysters, Ostrea edulis, were observed after exposure to TBT for 75 days, at a concentration of 0.24 μg/L, a delay in changing sex male to female was observed and larval production was completely inhibited. This phenomenon called "imposex," which can result in females with a penis, was detailed in the mid-eighties (FERNANDEZ et al. 2002).

As a result, by the end of this decade, countries like France, United Kingdom, United States and Japan, restricted the use of TBT paints. One of the first actions was to ban the use of TBT on vessels that were less than 25 meters in length.

In 1990, the Marine Environment Protect Committee (MEPC) belonging to the IMO adopted a resolution recommending that governments adopt measures to restrict the use of antifouling paints based on TBT.

In November 1999, the IMO Assembly agreed that a set of actions to be taken by MEPC, should ensure a global ban from 1 Jan. 2003, the application of the compounds of organic-tin, which act as biocides in systems of antifouling paint on ships, and a complete ban on the presence of such compounds by 1 Jan. 2008 (PROPELLER, 2000).

Importance of Antifouling

The use of the antifouling painting scheme has as a main purpose to avoid the extra fuel consumption due to additional drag force promoted by excessive fouling the hull of the vessel. It is estimated that the expense relating to the fuel in the shipping industry, is around 50% of the total cost of operation. The annual consumption of heavy oil Bunker type, related to the global commercial fleet, with a price of approximately US 100.00 per ton (1998), was estimated at 180 million tons. Biofouling can lead to an increase in fuel consumption of up to 40%, which would increase annual spending in over 7.2 billion dollars. This also implies an increase in a release to the atmosphere of 210 million tons of $CO_2$ and 5.6 million tons of $SO_2$ (PROPELLER, 1998).

A parallel problem to fuel consumption, which draws attention to the need to control biofouling, is the transfer of marine species, components or presents in the biofouling of shells, among the movements of vessels. Although quantitatively smaller compared to transfer of ballast water, organisms transferred by the hooves and anchors are also factors of environmental concern (NRC, 1996).

In Australia, the existing fouling on the hulls of vessels was seen as the main vector of introduction of exotic species in their territorial waters in the late $19^{th}$ century and throughout the $20^{th}$ century (Lewis, 2001a, b).

In the United States, the European zebra mussel, Dreissena polymorpha, infested about 40% of waterways of that country, implying spending that, according to some analysts, ranging from hundreds of millions to a billion dollars in control measures between 1989 and 2000 (http://www.greatlakes.net/envt/flora-fauna/invasive/zebra.html).

In New Zealand, research conducted by the National Institute of Water & Atmospheric Research have shown that at least 150 species of marine organisms have been introduced into its waters, and one new species every year, brought by vessels that visits their ports. It is estimated that 69% of the recorded species have been introduced by the hulls of vessels (NIWA, 2002).

In Brazil, the introduction of invasive species Limnoperna. fortunei, known as the golden mussel, was made through the ballast water of vessels that crossed the River Plate Basin. However, the scattering by the Paraguay River and the internal waters have been made mainly by the hull of vessels of different types and sizes.

The proliferation of the golden mussel has caused other problems, like the clogging of pipes and pumps. The observed economic impacts are huge, especially for industries that depends on the uptake of water directly from rivers, lakes and ponds, as dams and water supply companies to urban areas.

Antifouling Systems on Ships

Replacing the TBT

There is no use thinking of shipping, without the use of a defense mechanism against biofouling. Despite the wide range of applicability procedures tested with antifouling applicability, such as: paint base metals like copper and zinc, application of electric current, magnetic fields, radioactive paints with Thallium 204 and Technetium 95, the two most promising alternative systems to the use of TBT are the paint schemes called "fouling-release" and that employ-based paints non-toxic compounds, including natural biocides in this segment (Yebra et. al., 2004).

While some systems "fouling-release" are already available in the market, the development of an efficient product based on natural biocides seems still some way off.

Self-Cleaning System. "Fouling-Release"

The paint system called "fouling-release" can be considered as true non-stick systems, mainly using fluorinated polymers or silicon in their composition (BRADY, 2000). Fluorinated polymers such as polytetrafluoroethylene (PTFE), and the greater difficulty of handling and application, often suffer chemical rearrangements on the surface in contact with polar environments, losing its characteristics of non-wetting, which limits its commercial application. Their uses in the works vivid paintings of vessels need a way to stabilize the surface, and research to eliminate this obstacle is being sought, particularly with the use of semi fluorinated copolymers (Youngblood, 2003, Hayakawa et al. 2000; XIANG et al., 2000).

Systems using silicone are rubbers or elastomers primarily based on polydimethylsiloxane (PDMS) and have been developed since the sixties.

In the United States, Edward Robbart obtained a patent in 1961 (ROBBART, 1961) and Alexander Milne captured another in 1977 (MILNER, 1977). Soon after the patent has been obtained by Milne, the focus of research and development of antifouling turned to the TBT-copolymer systems, another survey of Milne, who at that time was getting a great commercial success. With this, the technology of self-cleaning paints "fouling-release", was left out (ANDERSON et al., 2003).

In the early eighties, when the environmental problems associated with TBT began to appear, researchers resumed their attention to research programs based on "fouling-release" paints.

These systems are usually free of biocides or in composition with non-toxic, making them environmentally attractive. While allowing the organisms from attaching to the hull when the vessel is stopped, at speeds over 20 knots, occurs the detachment of such organisms leaving the living works free of biofouling.

The performance of such schemes is based on three properties:

a) Surface energy, which controls the ability of a surface to cling to each other. Low-energy produces minimization of the adhesion strength of fouling;

b) The elastic modulus of the painting, which influences the mechanism of the junction between the surface and fouling organisms. Lower elastic modulus values imply weaker adhesions and, c) Thickness of painting, which is related to the release mode of the body surface. Guests staying exfoliation or peeling.

In general, schemes using fluorinated polymers act by peeling while working by using silicon exfoliation, which requires less energy to occur (LEWIS, 2002; BRADY, 2001e 1999).

Although this system shows high efficiency for high-speed craft, are chemically durable and free of biocides; its cost and its lack of efficacy for vessels of low speed or high speed and with little movement, and fixed structures, have limited its use until the present (PROPELLER, 1998).

Despite the efficiency of the paint schemes currently used, with silicon compounds to be smaller than those containing TBT, much has been researching in such materials because of its apparent non-toxicity and especially its availability. Compounds such as fluorosilicon containing pending groups in fluoroalkyl based on silicone, has demonstrated better self-cleaning characteristics compared to commonly used polysiloxane (GRULAN et al. 2004; MERA and WYNNE, 2001).

Natural products for use as antifouling, obtained from plants, insects and marine organisms have been investigated and several patents have been requested. Henry Hovde and colleagues, received a patent in 2001 which is based on the use of juvenile hormone, found among insects, which demonstrated biocide action against barnacles (HOUVE et al., 2001).

Lars Bohlin and colleagues, received a patent in 2004 that specifies the use of a mixture of peptides of the family "cyclotides," a new class of proteins extracted from the plant (*Viola odorata*) http://www.cyclotide.com, which presents beyond well action as antitumoral (LINDHOLM, 2002), a potential action against antifouling barnacles (BOHLIN et al., 2004).

Use of quaternary ammonium compounds (SUSIC, 2004), terpene derivatives (MATIAS, 2001) and vitamins (BONATI, 2001) have also been researched and patented, but not yet marketed.

Nontoxic Compounds

Due to the banning of the antifouling paint schemes using the TBT and the level of environmental pressure over this issue, several theoretically non-toxic products have been incorporated into paints and tested for their actual effectiveness and non-toxicity. Although the antifouling properties of many of the products surveyed are not fully evaluated in the marine environment, many builders and vessel owners have expressed interest in using an non-toxic antifouling paint and which is relatively not expensive, which is reflected application in low cost and high lifetime.

The capsaicin, natural compound non-toxic and irritating, responsible for the burning of black pepper and has been used as an animal repellent, can be effective against aquatic organisms that have a direct contact to the painted substrate (RACE and KELLY, 1994) and research at the University of Akron, Ohio, U.S., have been conducted to evaluate their action as antifouling in the marine environment (NEWBY, 2002).

Laboratory tests using tannins obtained from plants of the genus *Mimosa pudica* "mimosa", *Castanea dentata* "American chestnut" and *Schinopsis brasiliensis* "quebracho or braun" (STUPAK et al., 2003) and extracts of algae, *Bifurcaria bifurcata*, and sponge *Raspaciona Aculeata*, demonstrated to have potential bioactivity against the settlement of larvae of barnacles *Balanus amphitrite*.

The trans-8-shogaol compound isolated from the extract obtained from *Zingiber officinale* "ginger", and the new sesquiterpene 9-oxo-neoprocurcumenol obtained from *Curcuma aromatica* "saffron", traditional herbal medicine of eastern culture, demonstrated a high efficiency against membership mussels "Blue mussel" (ETON et al. 2003 and 2002).

In the search for products that could be used in combating biofouling, it was realized that many marine organisms do not have scale on its surface, while remaining completely under this infliction environment. These marine organisms have developed three main ways of acting against the infliction:

$1^{st}$) For the tolerance to the invading organism, where it suffers no damage to their vital processes of respiration, nutrition and locomotion;

$2^{nd}$) At impediment, can make the shift to a less damaging habitat or development of high rates of growth compared to the attacker, without jeopardizing their survival; and $3^{nd}$) For the defense itself, which may be mechanical, where surfaces with special structures hinder the settlement; physics, where surfaces with low surface energy prevents the adhesion, and chemical, with the secretion of metabolites harmful to predators or intruders (PEREIRA et al. 2003; ASSMANN et al, 2000; BERENBAUM, 1995, PENNINGS et al., 1994).

The possible chemical compounds released in the defense have generated great interest due to their possible use in the composition of an antifouling paint, and among the major compounds isolated that have antifouling activity are fatty acids, terpenoids, lipoproteins, glycolipids, phenols, lactones, peptides and sterols.

Even in the eighties, several trials have begun to be performed to evaluate the effectiveness of numerous natural products that could come to act as antifouling in marine paints preparation. The main approach has been the solvent extraction of body tissues and subsequent use of bioassays to assess the potential antifouling extracts (WATERMANN, 1997).

In 1981, at the University of Southern California, Backus et al. submerged wood panels impregnated with extracts obtained from marine sponges *Haliclona Rubens* and *Haliclona viridis*, to check its pissible antifouling action (BACKUS et al., 1983).

John Faulkner related 841 isolated compounds from marine organisms, in his review on the subject, covering the years from 1977 to 1998. Most of the records it was found metabolites obtained from marine sponges, including a compound called ceratinamine obtained from *Pseudoceratina purpurea*, had an antifouling action (FAULKNER, 2000, TSUKAMOTO et al., 1996).

In the extract from the marine sponge *Acanthella cavernosa*, collected on Yakushima Island in Japan, which inhibited the larval settlement and metamorphosis of barnacles *Balanus amphritite* were found compounds known as diterpenes kalihinenes (OKIN et al. 1995).

Glycerophospholipids Having Antifouling Activity.

In work conducted at the Department of Chemistry, University of Newcastle, Australia, were isolated and identified some lipids present in the extract from the marine sponge *Crella incrustans*, which showed marked antifouling activity in several clinical trials. These compounds were evaluated by means of RMN, IR and MALDI-MS, as belonging to the class of compounds glycerophospholipids being identical 1-O-hexadecyl-2-O-acetyl-sn-glycero-3-phosphocholine and 1-O-hexadecyl-sn-glycero-3-phosphocholine, glycerophospholipid analogs known as platelet aggregating factor.

The glycerophospholipid known as platelet activating factor is a potent biological mediator produced by various types of cells, which triggers various physiological responses in different cell types even at very low concentrations, $10^{-12}$ to $10^{-9}$ M (VENABLES et al. 1993, PRESCOTT et al. 1990).

This compound was elucidated simultaneously by groups of teachers Donald Hanahan, Department of Biochemistry, University of Texas, and Fred Snyder, Division of Medical Sciences, Oak Ridge, Institute of Nuclear Studies—Tennessee, which conducted an independent investigation of anaphylaxis in rabbits where platelets were activated, and testing of potential anti-hypertensive rats in a lipid (BLANK et al., 1979). After its structure is understood, a new field of research was opened, primarily targeting medical research (VENABLE et al., 1993).

The factor name aggregating to platelets although incorrectly used, because it describes only one of several effects that this substance causes, remained tied to the chemical structure of the compound being used extensively throughout the literature.

PAF and Lyso-PAF refers respectively to the "1-O-alkyl-2-acetyl-sn-glycero-3-phosphocholine," and "1-O-alkyl-sn-glycero-3-phosphocholine" without bond with the length or degree of unsaturation of the alkyl group, structurally related compounds can be labeled as PAF analogs.

The glycerophospholipids known as platelet aggregating factor shows phylogenetic conservation existing in various positions on the evolutionary scale, being present or being generated in a wide variety of organisms such as bacteria, protozoa, fungi, plants, invertebrates and vertebrates, including mammals. Since its composition in biological samples, consisting mainly of a mixture containing alkyd groups with 16 and 18 carbons in position sn-1 (McINTYRE et al. 1999).

Studies have also shown that PAF analogues such as synthetic glycerophospholipids "1-O-octadecyl-2-O-methyl-sn-glycero-3-phosphocholine," known as "Et-18-OCH$_3$ or Edelfosine," promotes a wide range of antitumor activity, and that unlike other drugs, this phospholipid does not affect the DNA of cells under treatment, but acts selectively on the cell membrane, disrupting the metabolism of lipids.

The link type ether present in carbons 1 and 2 make these alkyl-lyso-glycerophospholipid lipases resistant, thus allowing to accumulate in the membrane and other parts of mammalian cells, hindering their development or even taking it apoptosis (VAN DER LUIT et al. 2002; ZHOU et al., 1996).

Besides the compound edelfosine, other alkyl glycerophospholipids and some alkyl-phosphocholine have also presented a cytotoxic action in vivo and in vitro, especially against protozoa, where the studies on such compounds, although not yet fully understood, suppose mechanisms involving damage to the membrane plasma and cell signaling, with the commitment of many cellular metabolism (VERMA and DEY, 2004; PARIS et al., 2004, CROFT et al. 2003; SEIFERT et al., 2001).

Other PAF analogs with radical change in the position sn-1 or sn-2, have also been tested and alkyd radical substitutions in sn-1 by an acyl group and the acetyl radical in the sn-2, for propionyl butiril or have demonstrated a reduction in biological activity of these analogs (TOKAMURA et al. 2000, VENABLE et al., PRESCOTT et al. 1990; TOKAMURA et al. 1989). Similarly, a greater number of methylene groups between the phosphorus atom and nitrogen atom, or the absence of oxygen bound in sn-1 or sn-2, also cause a decrease in activity of these analogues.

The proposed use of such PAF analogues as antifouling agent, based on what happens in other cell types widely used in medicine and pharmacology (MARATHI et al. 2001; BOTITSI et al., 1998, VENABLES et al 1993), based on the possibility of triggering an antagonistic or inflammatory reaction in the cells of the fouling organisms into contact with such products.

Biocidal Activity.

The glycerophospholipids 1-O-octadecyl-2-O-methyl-sn-glycero-3-phosphocholine and 1-O-hexadecil-2-O-methyl-sn-glycero-3-phosphocholine have some special properties linked to its molecular structure. They are amphiphilic compounds possess a hydrophilic and a hydrophobic site, and zwitterionic, in example, have positive and negative charges (radical bipolar) in its structure, and also have low molecular weights PM ~500 Daltons.

These properties are important, when confronted with the EPS diffusion and the potential pathways for uptake by microorganisms. Due to its hydrophobic site, alkyd saturated long chain attached at one end of the molecule, these compounds can be easily absorbed through the lipid bilayer component of the containment cell and plasma membrane of the organisms.

Because they are amphiphilic molecules and have low molecular weight (MW<1000 Daltons), have a good potential to diffuse into the biofilm, and this same feature can also allow passage through a transmembrane protein present in the cell envelope and the plasma membranes, as some these proteins, called Porins have low specificity and generally allow the diffusion of hydrophilic molecules with MW less than 600 Daltons.

Another important factor is that these compounds are PAF analogues without acyl radical type in the sn-2 position, which allows them to act as signaling molecules, when in contact with or absorbed by microorganisms and not suffer the termination of its agonist action of PLA$_2$ enzymes, possibly existing ones. So, unfortunately they will accumulate in the casing wall or inside the cells, triggering an adversarial process of cellular response, which inhibit the development or destroy the microorganism.

Several patent documents describe the use of phospholipids with antimicrobial/antifouling activity.

The document U.S. Pat. No. 4,775,758 describes phospholipids that possess antitumor and antifungal activity, where the phosphate is linked to the central carbon of glycerol.

The document U.S. Pat. No. 5,118,346 describes quaternary ammonium compounds that are useful in antifouling compositions.

The document EP 752 997 describes cationic phospholipids that are useful in the distribution of drugs and nucleic acids in cells containing groups bonded carbon to oxygen of the phosphate group.

The document WO 98/47593 describes compounds that prevent fouling of vinyl monomers in petrochemical refining processes, where the compounds containing groups bonded carbon to oxygen of the phosphate group.

The present invention differs from the compounds mentioned above by an acyl group has only the hydrophobic portion of the molecule and a quaternary ammonium group, linked to the phosphate group.

Thus, the compounds of the present invention are new, facing the prior art, and inventive, by the structure is not even suggested in these documents.

BRIEF SUMMARY OF THE INVENTION

In a first aspect, the present invention provides a biocidal compound derived from lecthins.

It is an object of the invention to provide a biocidal compound having a structure according to formula (I):

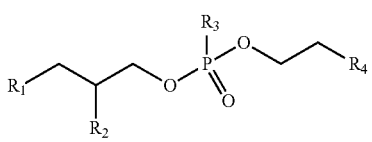

wherein:
R1 is a hydroxyl group or an O-acyl group containing from 2 to 22 carbon atoms, comprising from 0 to 3 instaurations;
R2 is a hydroxyl group or an O-acyl group containing from 2 to 22 carbon atoms, comprising from 0 to 3 instaurations;
R3 is OH or O$^-$; and
R4 is [N$^+$(CH$_3$)$_3$] or [N$^+$H(CH$_3$)$_2$].

It is an additional object of the invention to provide a process for the production of a compound according formula (I) above, comprising the step of reacting a compound of formula (II)

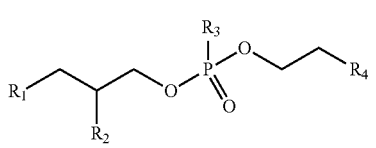

wherein:
R1 is an O-acyl group containing from 2 to 22 carbon atoms, comprising from 0 to 3 instaurations;
R2 is an O-acyl group containing from 2 to 22 carbon atoms, comprising from 0 to 3 instaurations;
R3 is OH or O$^-$; and
R4 is [N$^+$(CH$_3$)$_3$] or [N$^+$H(CH$_3$)$_2$], with sodium methoxide in methanol.

In a second aspect, the present invention provides a anti-fouling composition comprising a biocidal compound derived from lecthins.

It is an object of the invention to provide an antifouling composition comprising:
a) a biocidal compound structure according to formula (I):

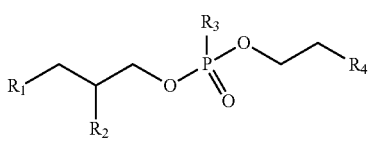

wherein:
R1 is a hydroxyl group or an O-acyl group containing from 2 to 22 carbon atoms, comprising from 0 to 3 instaurations;
R2 is a hydroxyl group or an O-acyl group containing from 2 to 22 carbon atoms, comprising from 0 to 3 instaurations;
R3 is OH or O$^-$; and
R4 is [N$^+$(CH$_3$)$_3$] or [N$^+$H(CH$_3$)$_2$], and
b) an acceptable vehicle.

It is a further object of the invention to provide a process for the production of a biocidal compound comprising the step of adding a compound of formula (I) above and an acceptable vehicle.

In a third aspect, the present invention provides a method for preventing fouling on surfaces that come into contact with fresh and/or salted water.

It is an object of the invention to provide a method to prevent fouling in surfaces, comprising the step of coating the surface susceptible to fouling with an antifouling composition comprising a compound according to general formula (I) above.

It is an additional object of the present invention to provide a method to turn a surface into an antifouling surface comprising the step of coating a surface susceptible to fouling with a composition comprising a compound according to general formula (I) above.

It is a further object of this invention to provide a surface coated with a compound according to general formula (I) above.

DETAILED DESCRIPTION OF PREFERRED EMBODIMENTS

Figure 1A:
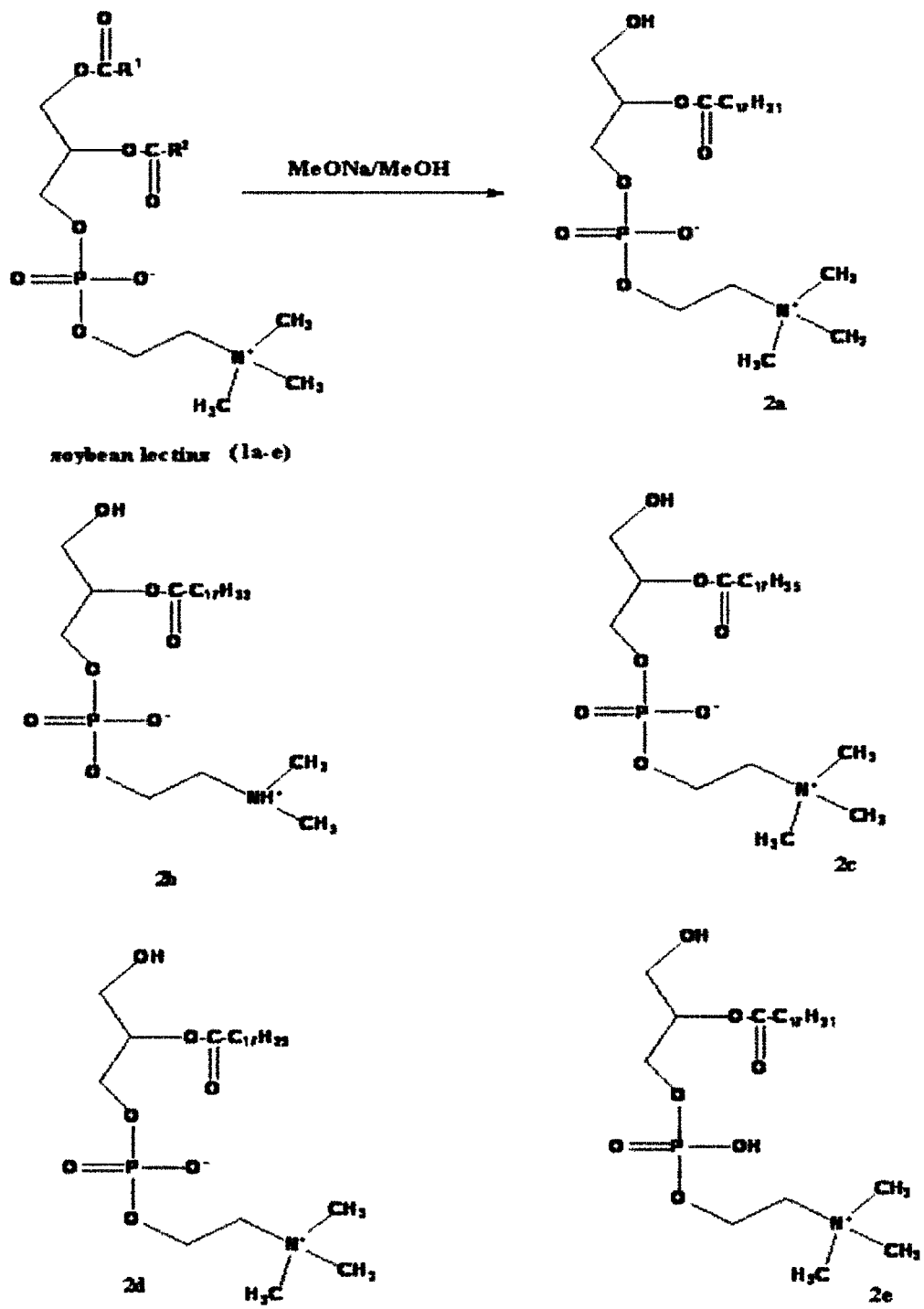
FIGS. 1A and 1B represent the products with biocidal activity and repellent (2a-j), obtained by the reaction of lecithin (1a-e) with sodium methoxide in methanol.
Figure 1B:
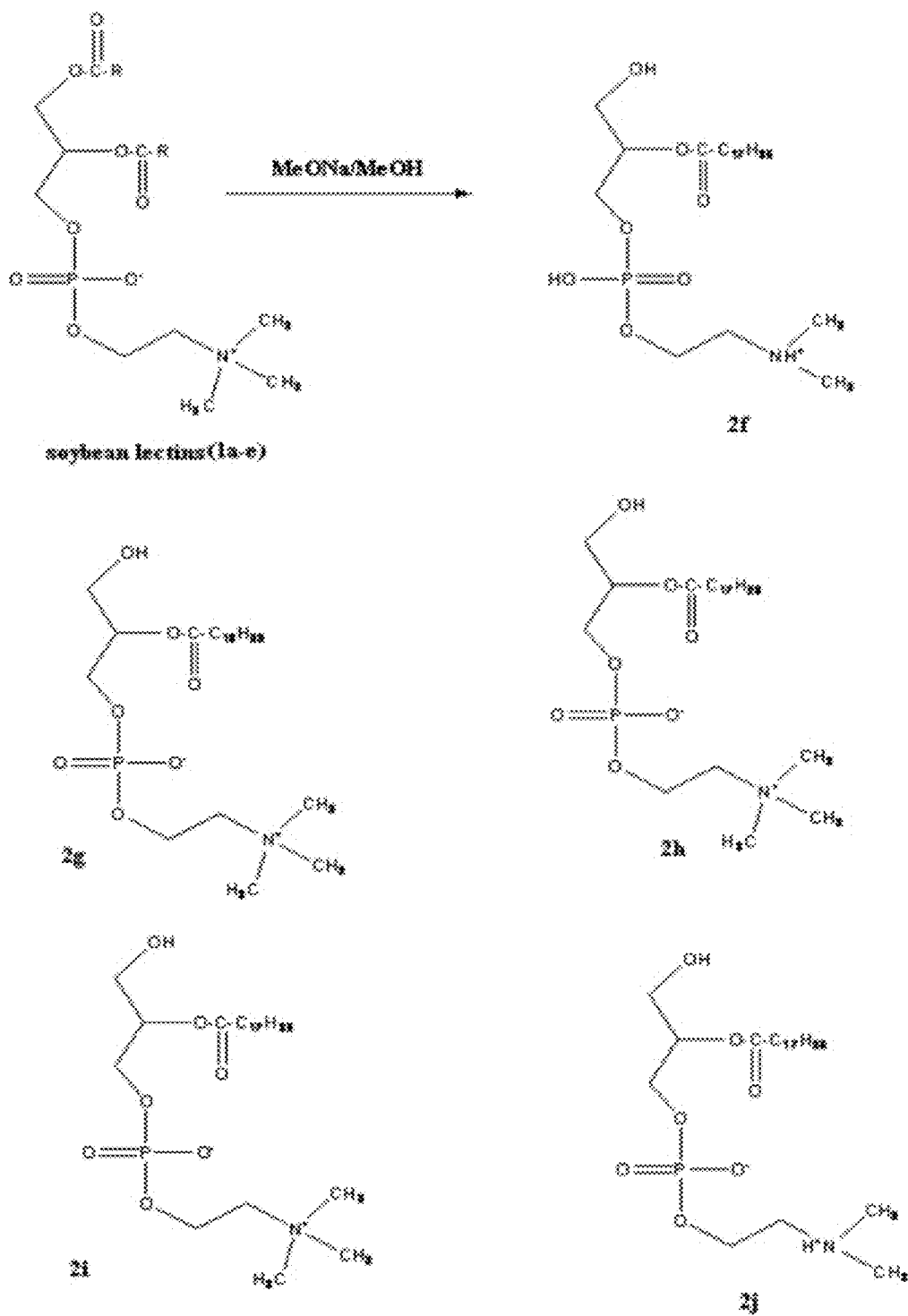
Figure 2A:
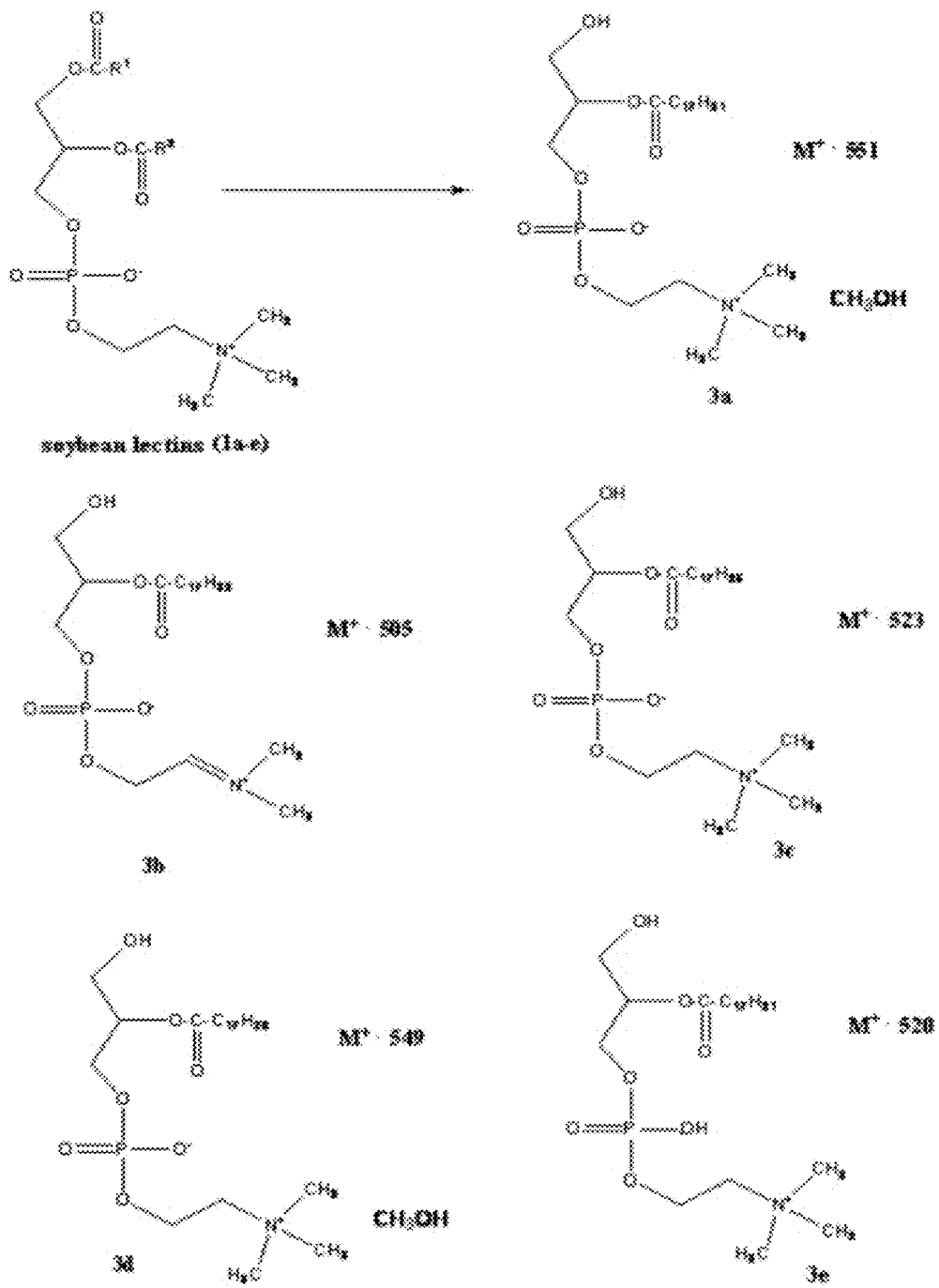
FIGS. 2A and 2B represent the ions observed (3a-j) in mass spectrometry for in these structures, some being detected in the form of adducts associated with solvents or protons in experimental conditions described above.
Figure 2B:
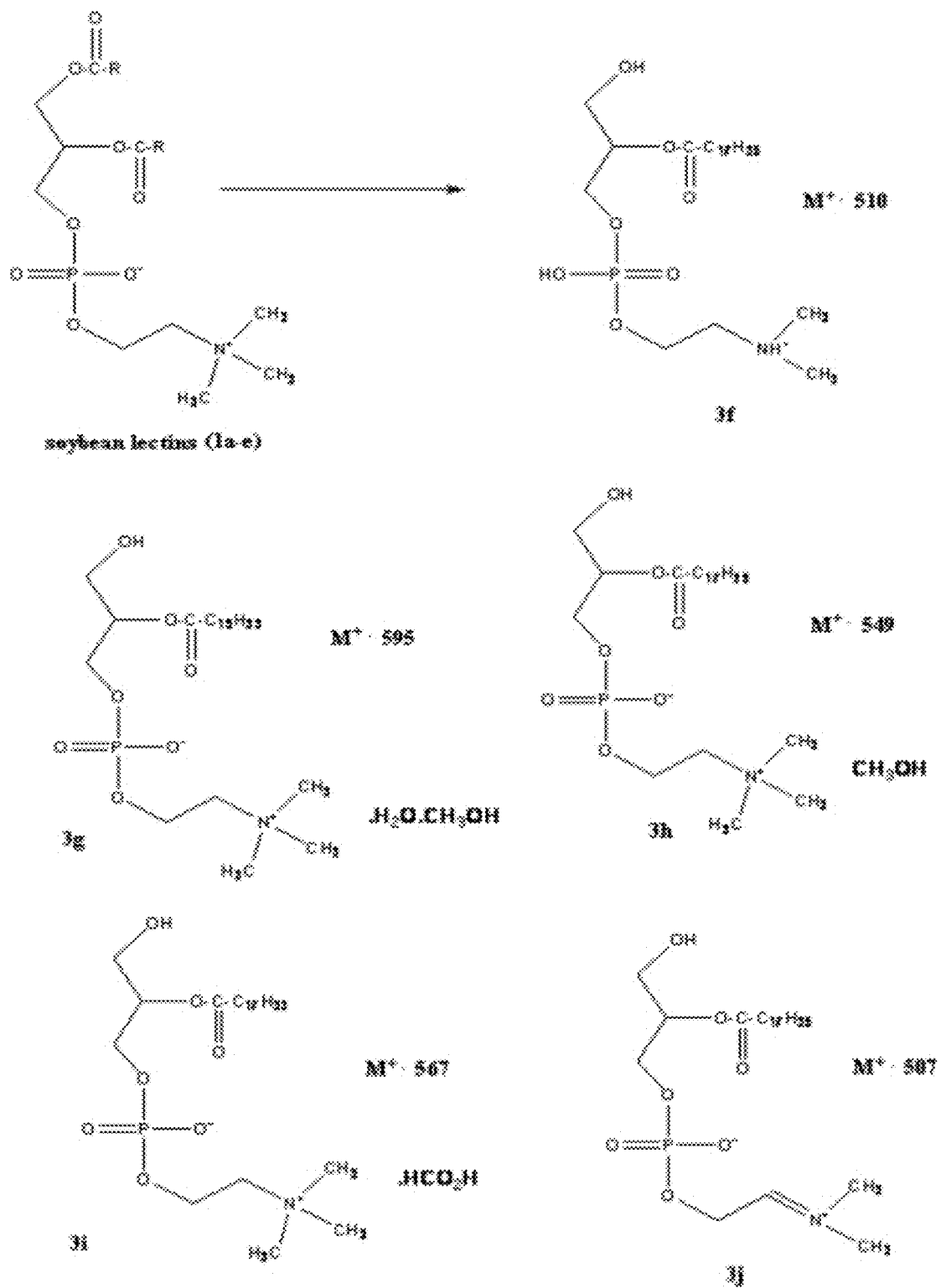

The examples described herein are intended only to illustrate some of the many ways of carrying out the invention and should not be viewed narrowly, but rather illustrative.

Biocidal Compound

The biocidal compound of the present invention have general formula (I):

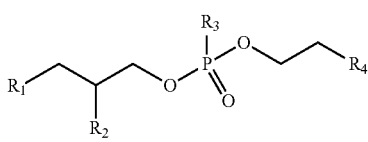

(I)

wherein:
R1 is a hydroxyl group or an O-acyl group containing from 2 to 22 carbon atoms, comprising from 0 to 3 instaurations;
R2 is a hydroxyl group or an O-acyl group containing from 2 to 22 carbon atoms, comprising from 0 to 3 instaurations;
R3 is OH or O$^-$; and
R4 is [N$^+$(CH$_3$)$_3$] or [N$^+$H(CH$_3$)$_2$].

Preferably, R1 is hydroxyl and R2 is an O-acyl group containing 2 to 22 carbon atoms, in particular, OC(O)C17 with 0 unsaturations, OC(O)C17 with an 1 unsaturation, OC(O)C17 with 2 unsaturations, OC(O)C17 with 3 unsaturations and OC(O)C19 with 2 unsaturations.

Process of Preparation

The process of preparation of the compounds of formula (I) comprising the reaction of compounds having formula (II):

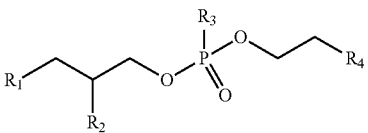

(II)

wherein:
R1 is an O-acyl group containing from 2 to 22 carbon atoms, comprising from 0 to 3 instaurations;
R2 is an O-acyl group containing from 2 to 22 carbon atoms, comprising from 0 to 3 instaurations;
R3 is OH or O$^-$; and
R4 is [N$^+$(CH$_3$)$_3$] or [N$^+$H(CH$_3$)$_2$], with sodium methoxide in methanol.

Preferably, the synthesis of chemical structures in accordance with the general formula (I), involves the treatment of lecithins with a solution of sodium methoxide in methanol prepared in situ during a long period of agitation at room temperature or heated as described in the experimental below. The compounds of formula (II) are preferably lecithin, particularly soybean lecithin. The byproducts of the reaction of sodium methoxide with the soybean lecithin, are the corresponding methyl esters (biodiesel) fatty acid constituents of these substances mixed with glycerophospholipids.

Chemically, lecithins are organic compounds rich in phosphorus, formed by polar lipid structures called phospholipids and nonpolar lipids (fatty acids). These compounds are found in all living cells of animals and plants allowing the proper functioning of vital organs.

The lecithins are essentially a natural biodegradable product, relatively stable at room temperature and hygroscopic, presenting emulsifiers own characteristics due to the complex chemical composition, being used in various industrial applications and for nutritional purposes.

The soybean lecithin (1a-e) employed in this invention have the following chemical structures are summarized below (Table 1), structurally characterized by mass spectrometry using a system of high-performance liquid chromatography (HPLC) coupled to a Shimadzu Prominence analyzer type of mass iontrap of Bruker (ESI-MSn) Esquire 6000:

TABLE 1

| Structure of Lecithin Used | |
|---|---|
| R1=R2= acyl group of fatty acid | % |
| 1a) Gamma homolinolenic Acid (C20:3) | 5.7% |
| 1b) Stearic Acid (C18:0) | 18.6% |
| 1c) Oleic Acid (C18:1) | 12.8% |
| 1d) Linoleic Acid (C18:2) | 54.0% |
| 1e) Linolenic Acid (C18:3) | 8.9% |

The product of this synthesis was incorporated into a base paint, with no biocide additives or biocides accessories, used in coating vessels, for an evaluation of antifouling activity in field trials in the Bay of Guanabara—Rio de Janeiro—Brazil. To this end, we used metal plates coated with an appropriate paint scheme often used for ships containing the ink prepared with the biocide synthesized.

Antifouling Composition

The antifouling composition of the present invention comprises:
a) a biocidal compound according to formula (I):

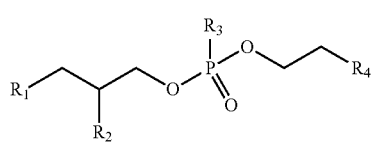

(I)

wherein:
R1 is a hydroxyl group or an O-acyl group containing from 2 to 22 carbon atoms, comprising from 0 to 3 instaurations;
R2 is a hydroxyl group or an O-acyl group containing from 2 to 22 carbon atoms, comprising from 0 to 3 instaurations;
R3 is OH or O$^-$; and
R4 is [N$^+$(CH$_3$)$_3$] or [N$^+$H(CH$_3$)$_2$], and
b) an acceptable vehicle.

The antifouling composition can be applied to the surface of many objects, especially those susceptible to fouling by being in constant contact, frequent or intermittent salt water and/or sweet. Examples of such surfaces include, with no limitation, ships, vessels, yachts, sailboats, rafts, submarines, ferries, speedboats, frigates, aircraft carriers, icebreakers, rowboat, sloop, and tug vessels. Other arrangements includes planks surfing, windsurfing, and water skiing. The surface can also be buoys, piers, breakwaters, oil platforms, fences, farming, fishing nets, and underwater cages. Other objects includes oxygen tanks and diving equipment, periscopes, rudders, propellers, and keels.

Beyond such surfaces, equipment connected the water treatment, desalination, hydroelectric plants, and food processing, membranes, filters, piping, valves, pumps, condensers, evaporators, heat exchangers and combinations thereof are considered suitable surfaces.

Membranes and filters are also considered suitable for coating surfaces according to the present invention. Industrial equipment such as pipes, valves, pumps, condensers, evaporators and heat exchangers are considered suitable for coating surfaces according to the present invention.

The antifouling composition of this invention comprises excipients commonly found for this type of composition in the prior art and can also contain other active antifouling known, such as copper oxides.

The amount of active antifouling composition of the present invention is from 10% to 60%. When combined with other assets, its concentration varies from $O_2$% to 20%. These assets can be antifungal, algaecides, pesticides and other compounds known from the prior art.

The composition further comprises binders such as polyvinyl chloride, acrylic resins, copolymer of vinyl chloride-vinyl acetate, rubber of acrylonitrile-butadiene-stireno, all systems of solvents or aqueous dispersions, when possible. In addition, organic pigments, inorganic pigments, dyes, insoluble in sea water may be present. Plasticizers, viscosity modifiers and other ingredients can be included as desired.

Preparation of the Composition Process

The process of preparation of antifouling composition of the present invention comprises the step of adding a compound of formula (I) above in an acceptable vehicle, also as described above.

The methods and stages of preparation are known from the prior art.

Method to Prevent Fouling

The method for preventing fouling on suitable surfaces according to the present invention comprises the step of applying an antifouling composition in a suitable surface, susceptible to fouling due to contact with fresh water and/or salt. After application of the composition, which forms a coating on the surface, it can be dipped in water.

Method for Making a Surface Antifouling

The method for making antifouling suitable surfaces according to the present invention comprises the step of applying an antifouling composition to the appropriate area.

EXAMPLE 1

Experimental Procedure

In a 2000 mL glass reactor with 5 joints of 24×40 equipped with a reflux condenser with cold water, coupled with a mechanical stirrer Eurostar Power b IKA WERKE, methanol is added to 1000 mL, 3.0 grams (0.13 atgs) of metallic sodium and 40.0 grams of soybean lecithin. The reaction mixture is left under agitation for 72 hours at room temperature or under heating 45-60° C. At the end of this period to extract the product, transfer the mixture to a reaction beaker then the solid residue is filtered by gravity on filter paper. In the next step this product is subjected to removal of volatile substances through the use of a desiccant glass Pyrex brand vacuum. The solid product was obtained in 33.4 g, resulting in a yield of 84% by weight. The resulting oil after complete evaporation of methanol to a mixture of methyl esters (biodiesel) with a mass in grams of 6 g, providing a yield of 15%.

The regioselectivity of the nucleophilic attack of the species represented by molecules of sodium methoxide to the carbonyl electrophilic center position of a soybean lecithin (1a-e) led to formation of desired products of type 1-hydroxy-2-O-acyl-sn-glycero-3-phosphocholine, (2 i).

In the presence of sodium methoxide in methanol to soybean lecithin (1d) underwent a regioselective hydrogen abstraction on the carbon alpha to the nitrogen quaternary phosphocholine chain, providing the corresponding iminium derived glycero phosphocholine (2b).

The derived 1-hydroxy-2-O-stearate-sn-glycero-3-phosphocholine (2c) can undergo a nucleophilic attack of the species in the methoxyl methyl quaternary nitrogen molecule generating the corresponding derivative (2f) and dimethyl ether. It is worth mentioning that the final structure 2f is formed in the presence of formic acid. This substance was used as a component of the eluent from the separation process using HPLC.

Finally, the abstraction of hydrogen attached to carbon vicinal phosphate 2c function, enabled by the presence of trimethyl ammonium leaving group in this molecule, derived form the olefin (2j), structurally characterized by mass spectrometry, represented in Scheme 1 (mechanistic proposed derived to obtain 1-hydroxy-2-β-stearate-sn-glycero-3-vinyl-phosphate (2 h) from 2c in the presence of sodium methoxide in methanol).

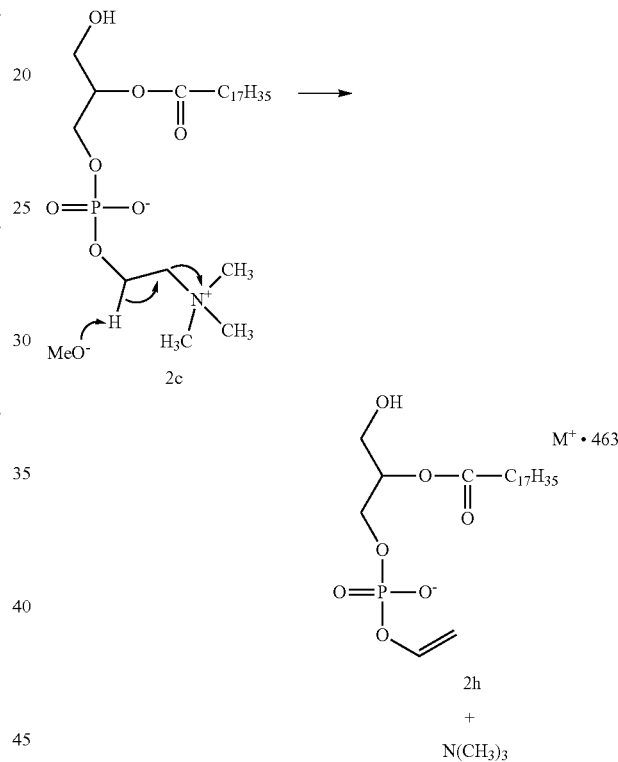

Scheme 1

Chromatographic Conditions

A system of high-performance liquid chromatography PROMINENCE SHIMADZU, with high-pressure pump, Rheodyne injector with handle 20 μl and column type C18, Thermo (5 μm), 250×2 mm, was used to separate the constituents of samples glycerophospholipids. As mobile phase used was a combination of isopropanol, water, methanol and ethyl acetate. The separation was achieved with a gradient starting with (40/15/40/05), maintained for 10 minutes at a flow rate to 0.1 ml/min, passing (25/05/50/20) for 15 minutes at a flow rate of 0.3 ml/min and maintained until final time of 30 minutes.

Mass Spectrometry

The synthesized glycerophospholipids were dissolved in a mixture of methanol/chloroform/water (2/1/1) and injected manually through a Rheodyne injector with handle 20 μl. The eluted components were directed to a mass spectrometer type iontrap through ESI, being evaluated in a positive way about their reasons for mass/charge. The molecular ions were then compared to the standards provided in the virtual library LIPIDMAPS (www.lipidmaps.org), seeking a preliminary indication and then subsequently isolated and fragmented in iontrap for viewing and confirmation of the fragments characteristic of the structures.

The liquid chromatography system was coupled online to a mass spectrometer type iontrap Esquire 6000 (Bruker Daltonics) equipped with an orthogonal eletronebulizer. The capillary needle was setada to −4.0 kV, nebulizer 30 psi with a nitrogen gas flow of 10 l/min at a temperature of 300° C. Helium gas was used for cushioning the trap, high vacuum of $1 \times 10^{-5}$ mbar, trap drive 59.1, octopolo RF 194.5Vpp, the Lens 1-5V, −60V to Lens 2, capillary exit 132.3 V, the skimmer 40V, 12V DC to Octopolo 1 and 2 Octopolo DC to 1.7 V.

EXAMPLE 2

Evaluation of the Antifouling Activity of Derivatives Type 1-Hydroxy-2-O-Acyl-Sn-Glycerophosphocholines (2a-j)

The synthesis product was evaluated using laboratory tests and field tests, and its possible use and effectiveness as a biocide antifouling substance against the settlement of marine micro-organisms present in the precursors and formation of biofilm. In addition, mass spectrometric analysis using HPLC coupled to electrospray ionization type iontrap spectrometer were used to elucidate the composition of glycerophospholipids obtained by synthesis.

Laboratory Tests

A small number of marine microalgae is considered important as fouling organisms, especially the Chlorophytes, Heteroconta (mostly Diatoms) and Rhodophyces, cyanobacteria are also often seen as primary colonizers.

In the Biofilm Laboratory IEAPM a test was conducted to test the activity of the product of synthesis in the growth of three microalgae species representing major groups of organisms present in microincrustation. We used a kind of Prasinoficea respectively, the *Tetraselmis striata*, of Chlorophytes the *Dunaliella tertiolecta* and of Diatom the *Skeletonema costatum*, originating in the Laboratory of Microalgae IEAPM.

The activity of the synthetic product was compared with copper sulfate ($CuSO_4$), one of the copper compounds used in antifouling paints, and the blank control test was used for the extraction solvent (methanol and dichloromethane and water).

All experiments were performed in triplicate. 15 ml of Culture Medium Conway were placed in test tubes and inoculated with $5.10^5$ Cells.ml$^{-1}$ of microalgae species, observing the exponential growth phase. The bottles containing the microalgae were placed in an incubator at 18° C. with a 12 h light 12 h dark (FIG. 10) and evaluated for its development.

In control tubes, in example, without the synthesis product and without biocide compound, solvent was added methanol, dichloromethane, water in the proportion 2:1:1. A series of tubes containing $CuSO_4$ (10 μg.ml$^{-1}$) was used as a standard. The cell growth was estimated daily for five days by direct counting of cells in a Hematocitometer from Neubauer.

Results of Laboratory Tests

Figure 3:
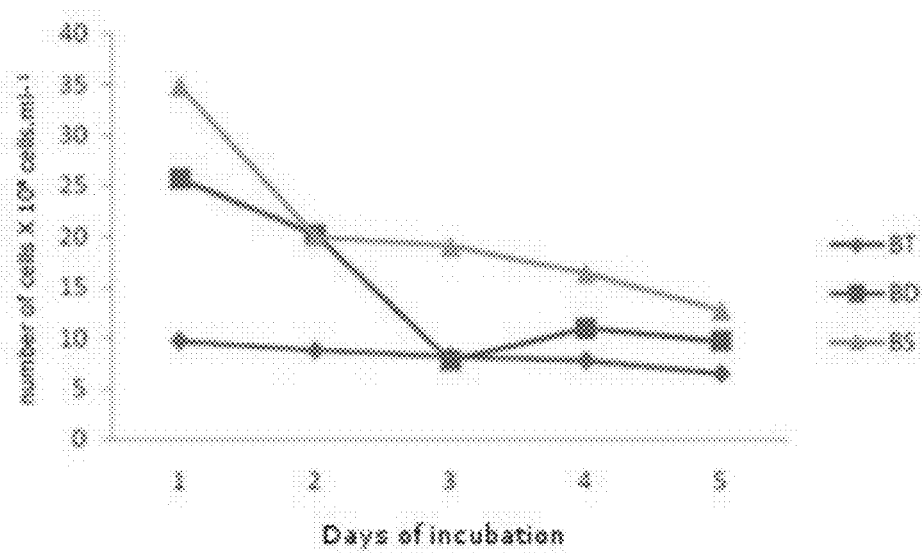
FIG. 3—Effect of White—B in the growth of microalgae after 5 days of incubation (BT—*Tetraselmis striata*, BD—*Dunaliella tertiolecta*, BS—*Skeletonema costatum*).
Figure 4:
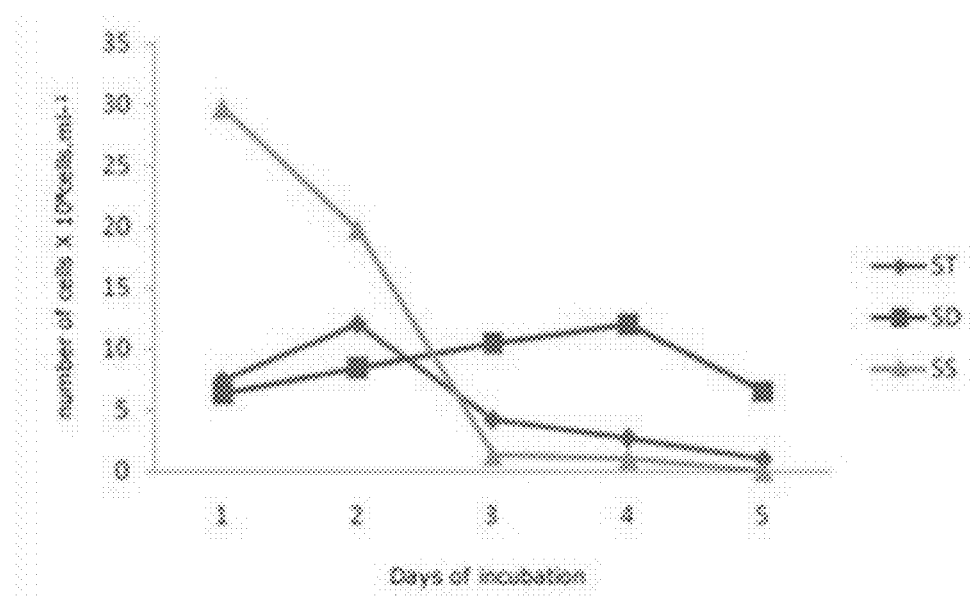
FIG. 4—Effect of "Substance Test"—S the growth of microalgae after 5 days of incubation (ST—*Tetraselmis striata*, SD—*Dunaliella tertiolecta*, SS—*Skeletonema costatum*).
Figure 5:
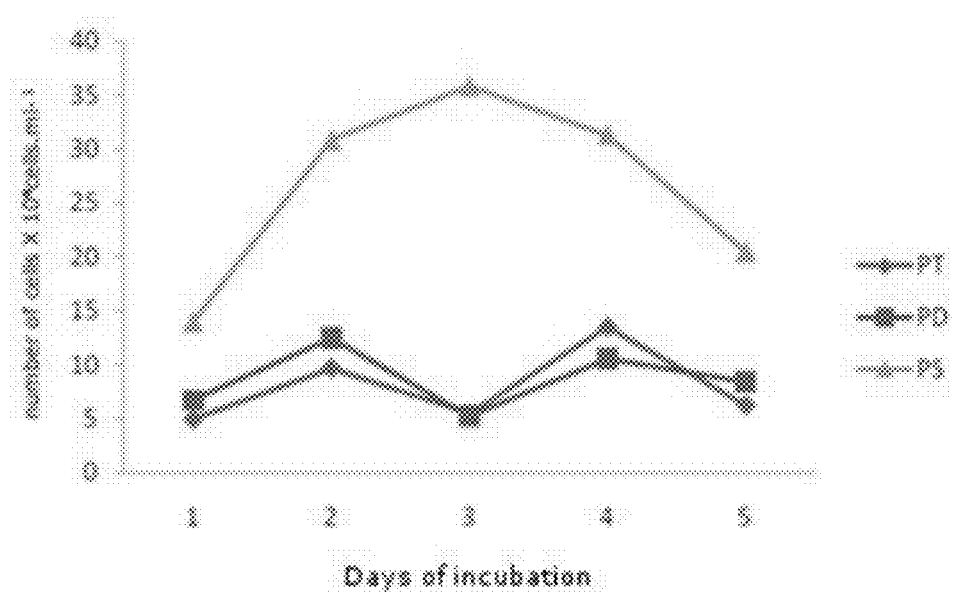
FIG. 5—Effect of Pattern—P (CuSO4) on the growth of microalgae after 5 days of incubation (PT—*Tetraselmis striata*, PD—*Dunaliella tertiolecta*, PS—*Skeletonema costatum*).
Figure 6:
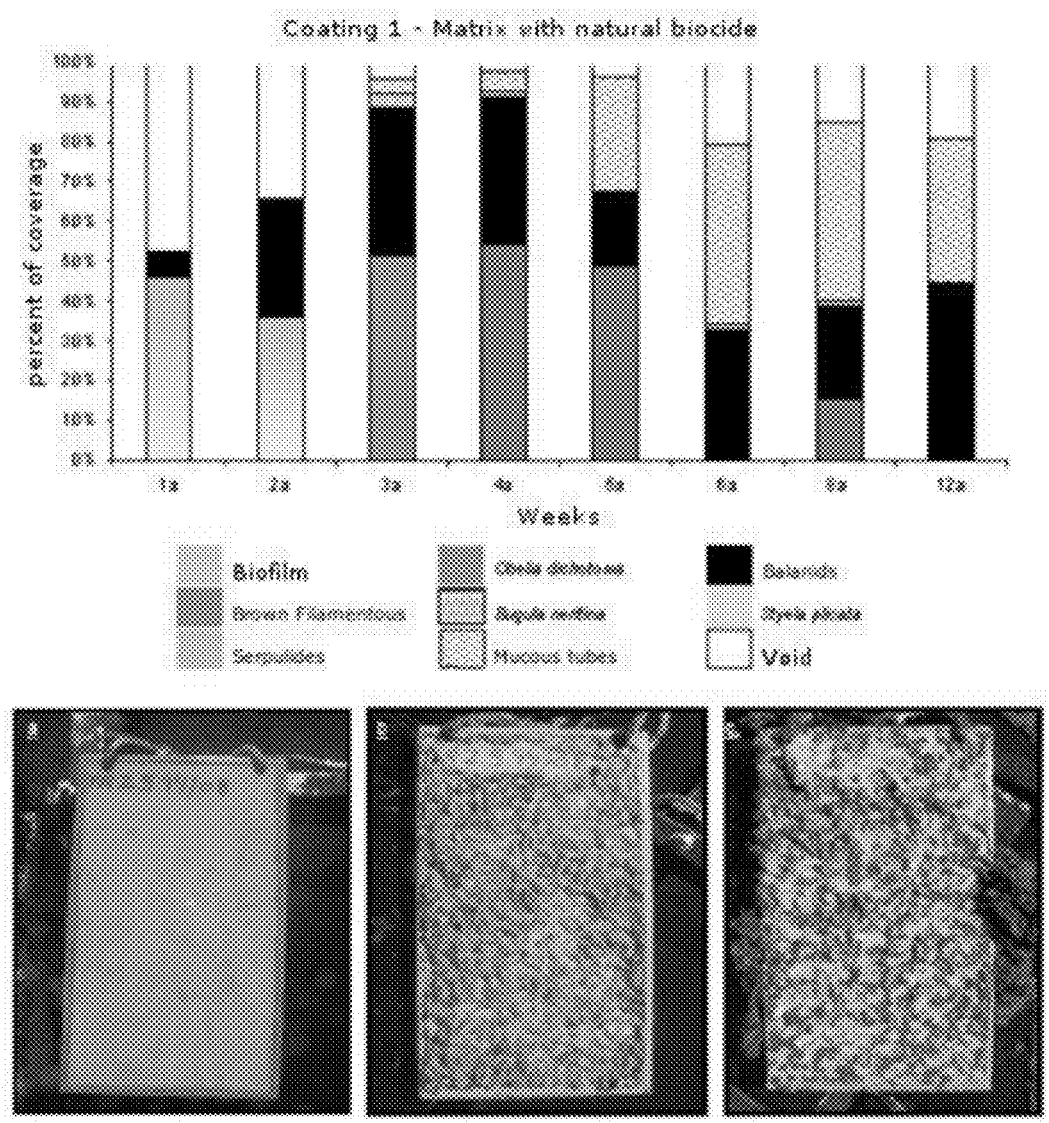
FIG. 6. Variation of the percentage of group coverage, fouling species and empty spaces. Photographs show the community development and the appearance of one of the bodies-of-proof treated with a Coating 1 (a) 1$^{st}$ week, (b) 4$^{th}$ week and (c) 8$^{th}$ week.
Figure 7:
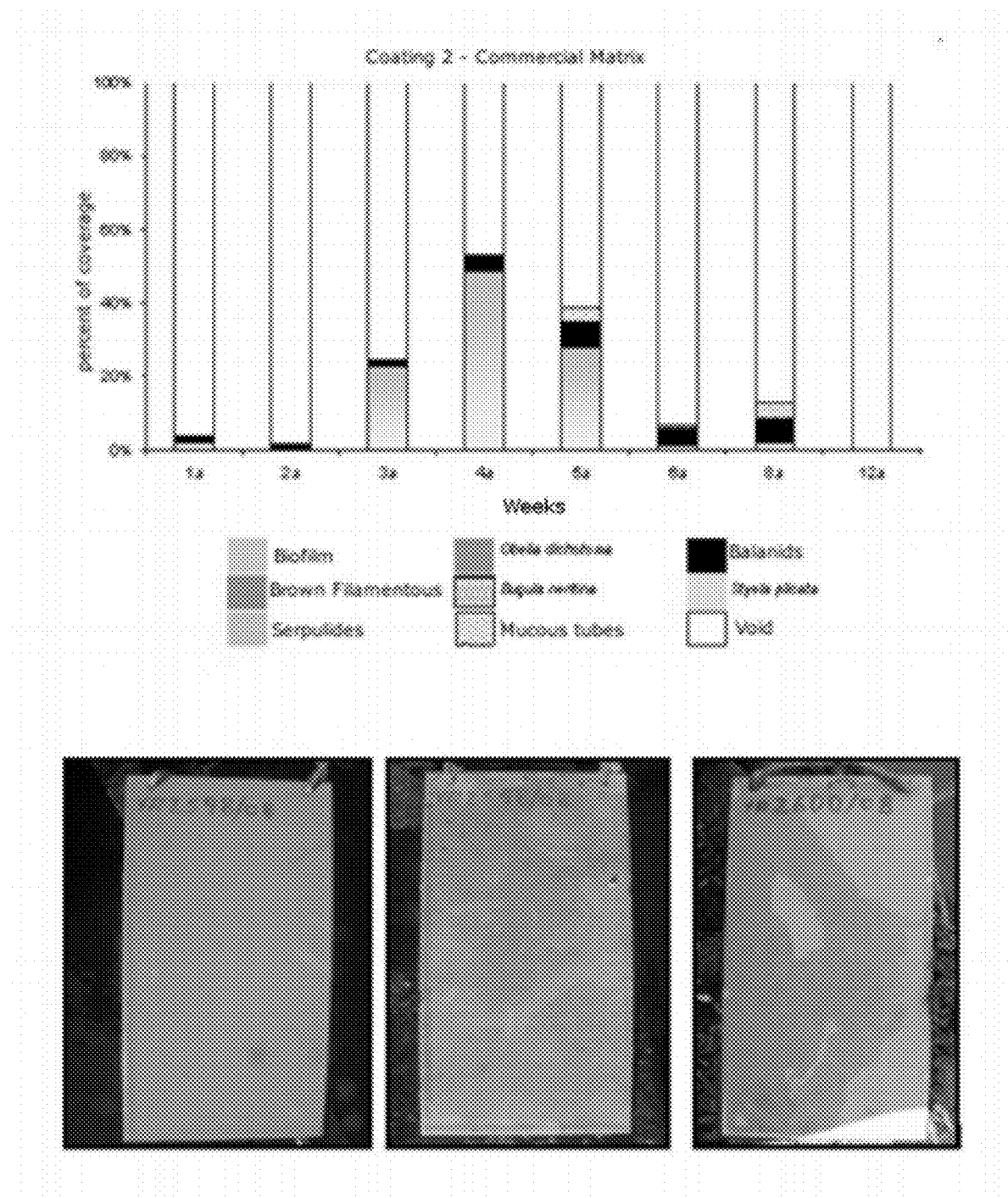
FIG. 7—Variation of the percentage of group coverage, fouling species and empty spaces. Photographs show the community development and the appearance of one of the bodies-of-proof treated with a Coating 2 (a) 1$^{st}$ week, (b) 4$^{th}$ week and (c) 8$^{th}$ week.

FIGS. 3, 4 and 5 shows that the synthesis product displays a high level of antifouling activity against the growth of the Diatom *Skeletonema costatum* and appears to be active against the growth of Prasinoficea *Tetraselmis striata* and less active against the development of Chlorophytes *Dunaliella tertiolecta*. It is important to observe the activity of antifouling product synthesis, especially against the growth of Diatom species, because this group represents a major component of the biomass of organisms microincrustation.

Field Tests

The biocide compound according to general formula (I) was incorporated by the International Paint, into a resin antifouling paint, commercially available and used to make the coating of carbon steel plate measuring (15×27) cm used in tests the field. The plates were immersed directly into Guanabara Bay, Rio de Janeiro—Brazil, using floating rafts and evaluated weekly for a consecutive period of three months, the presence of macro-fouling organisms and 8 months as the stability of the successional process of biofouling.

Four different coatings were applied in the bodies-of-test with three replicates of each:

1$^{st}$) Coating 1—Base paint wherein the main biocide (copper oxides) was replaced by natural biocide (product of synthesis according to general formula (I)), without the presence of other additives biocides (boosters), and 2$^{nd}$) Coating 2—Antifouling commercial paints from International Paints comprising copper oxides and biocidal additives (boosters), and 3$^{th}$) Coating 3—Base paint wherein the product synthesized according to general formula (I) was used as a biocidal worn accessory copper oxides, but replacing the conventional biocidal additives (boosters), and 4$^{th}$) Coating 4—Control—Base paint without biocide.

The analysis of the fouling community outreach for 3 months and a half was estimated by means of digital photography, the two sides of each body-of-evidence (FIGS. 6 to 9). In photo technique was applied to points of intersection (FOSTER et al., 1991). To this end, the pictures were analyzed in the program Coral Point Count (CPCe) (KOHLER and Gill, 2006). The photos were subdivided into a grid of 100 sub-rectangles of (2×1) cm. 100 points of intersection were accounted for, recording fouling below the intersection points marked. The record of fouling organisms was done in the lowest possible taxonomic level, both for and macroalgae for invertebrates (Table 1). The macroalgae were grouped according to their morpho-functional type (filamentous, sheetlike cortical and macrophytes). Since invertebrates were recorded in large groups (balanids, serpulids, hydrozoans, bryozoans fouling) or species level. Treatment of nomenclature for organisms followed proposed by the Integrated Taxonomic Information System (http://www.itis.usda.gov).

TABLE 1

Synopsis taxonomic and morpho-funcional types and/or groups that were included in the reported species.

| Kingdom | Division/Phylum | Class | Order | Family | Type/Group |
|---|---|---|---|---|---|
| Plantae | Chlorophyta | Chlorophyceae | Ulvales | Ulvaceae | Foliaceous |
| | Phaeophyta | Phaeophyceae | Ectocarpales | Ectocarpaceae | Brown Filamentous |
| | Rhodophyta | | Ceramiales | Ceramiaceae | Red Filamentous |

TABLE 1-continued

Synopsis taxonomic and morpho-funcional types and/or groups that were included in the reported species.

| Kingdom | Division/Phylum | Class | Order | Family | Type/Group |
|---|---|---|---|---|---|
| Animalia | Cnidaria | Hydrozoa | Hydroida | Campanulariidae | *Obelia dichotoma* (Linnaeus, 1758) |
|  | Anthozoa |  | Actiniaria | Actiniidae | Anemones |
|  | Annelida | Polychaeta | Canalipalpata | Serpulidae | Serpulides |
|  | Arthropoda | Cirripedia | Thoracica | Balanidae | Balanids |
|  | Ectoprocta | Gymnolemata | Cheilostomata | Bugulidae | *Bugula neritina* |
|  | Chordata | Ascidiacea | Stolidobranchia | Styelidae | *Styela plicata* |

Results of Field Tests

In all treatments was observed at initial presence of biofilm and subsequent recruitment of macro-fouling organisms.

In a coating 1, containing the product of synthesis, was observed the presence of biofilm in the first two weeks (FIG. 6), and *Obelia dichotoma*, *Bugula neritina* and Balanids in the next few weeks. The presence of empty space (without fouling organisms) was observed throughout the successional process from the first week, ranging from 10-50% coverage.

In the coating 2 with commercial paint (FIG. 7), was observed the presence of empty space in most of the study. However, it was verified the presence of biofilm-forming organisms and macro-fouling organisms between the third and eighth weeks.

Figure 8:
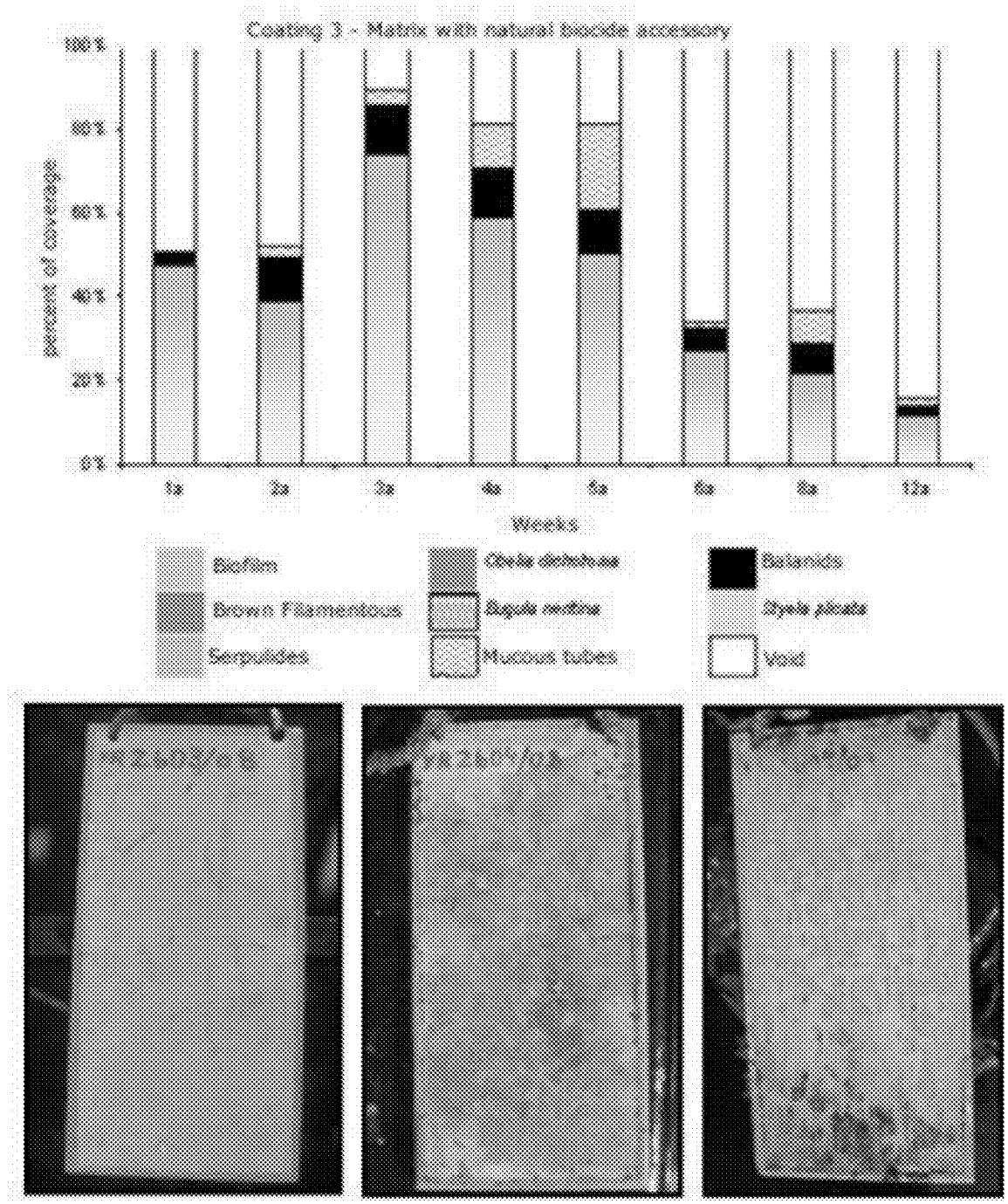
FIG. 8—Variation of the percentage of group coverage, fouling species and empty spaces. Photographs show the community development and the appearance of one of the bodies-of-proof treated with a Coating 3 (a) 1$^{st}$ week, (b) 4$^{th}$ week and (c) 8$^{th}$ week.

Results of the coating 3 were similar to those in treatment 2, only in more coverage (FIG. 8).

Figure 9:
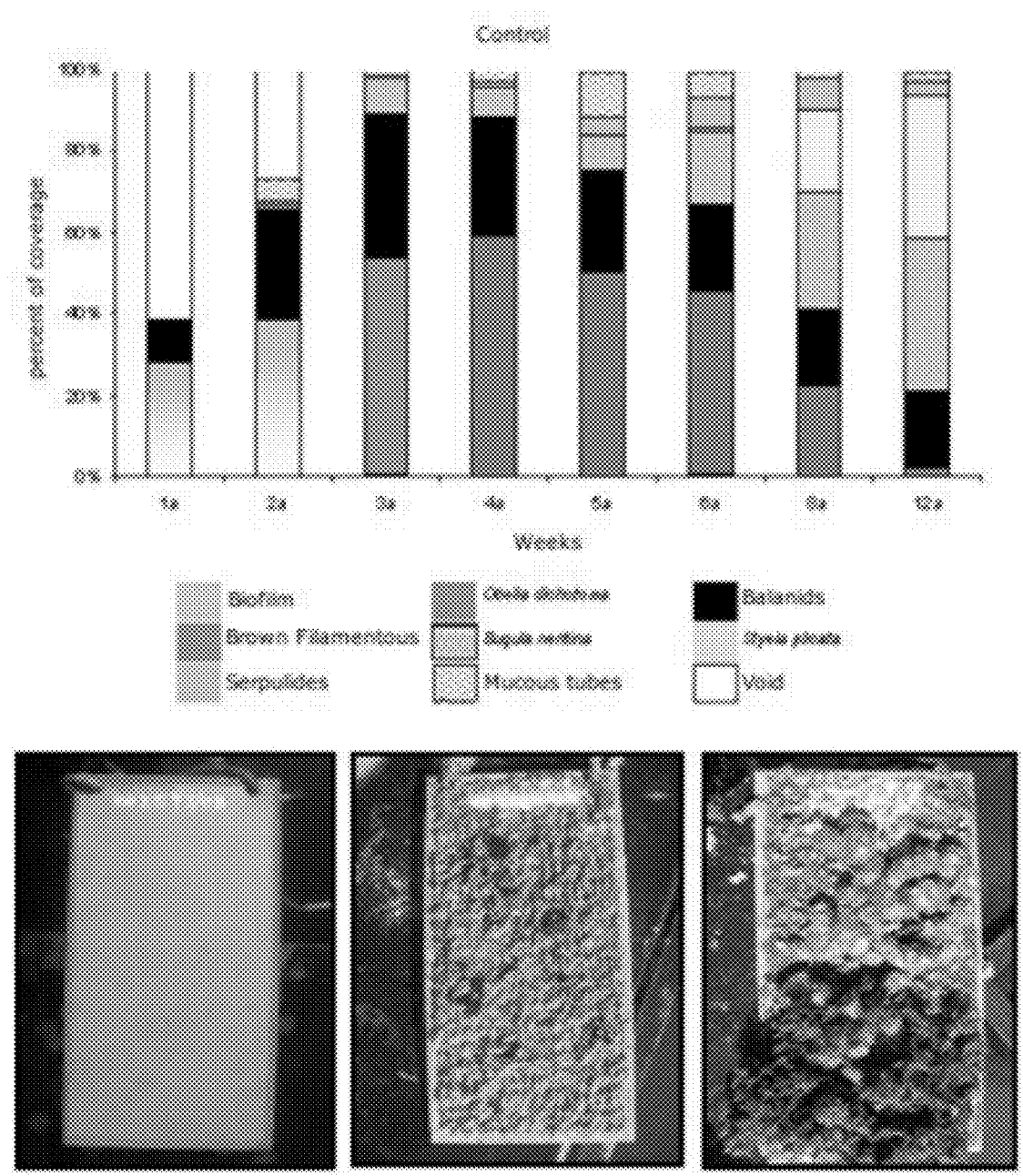
FIG. 9—Variation of the percentage of group coverage, fouling species and empty spaces. Photographs show the community development and the appearance of one of the bodies-of-proof treated with a Coating 4 (a) 1$^{st}$ week, (b) 4$^{th}$ week and (c) 8$^{th}$ week.

In the control treatment, coating 4, was observed a large presence of fouling organisms when compared with other treatments (FIG. 9).

In summary, was observed that the coating 1 (replacing the copper oxide synthesis by biocidal product in accordance with the general formula (I)), provided a significant reduction in coverage of fouling organisms when compared with the control (without biocide). Moreover, the coating 3 (replacement of accessories with the biocide biocides synthesis product in accordance with the general formula (I)) showed a better efficiency than treatment in a reduction of fouling organisms.

BIBLIOGRAPHIC REFERENCES

1 Allison, D. G. (1998). Exopolysaccharides production in bacterial biofilms. Biofilm. Vol. 3. http://www.bioline.org.br/bf. Accessed on 18 de Fevereiro de 2005.
2 Anderson C.; Atlar M.; Callow M.; et al. (2003). The development of foul-release coatings for seagoing vessels. Journal of Marine Design and Operations. Vol. B4, pp 11-23.
3 Arce, F. T.; Avci, R.; Beech, I. B.; Cooksey, K. E. e Cooksey, B. W. (2004). A live bioprobe for studying diatom-surface interactions. Biophysical Journal. Vol. 87, pp 4284-4297.
4 Assmann M.; Lichte E.; Pawlik J. R. and Köck M. (2000). Chemical defenses of the Caribbean sponges *Agelas wiedenmayeri* and *Agelas conifera*. Marine Ecology Progress Series. Vol. 207, pp 255-262.
5 Bakus G. J.; Evans T.; Mading B.; et al. (1983). The use of natural and synthetic toxins as shark repellents and anti-fouling agents. Toxicon (Suppl.). Vol. 3, pp 25-27
6 Balsinde, J.; Winstead, M. V. and Dennis, E. A. (2002). Phospholipase A2 regulation of arachidonic acid mobilization. FEBS Letters. Vol. 531, pp 2-6.
7 Batista W. R., Tese de Mestrado UFRJ (2006). Avaliação da Atividade anti-incrustante de Glicerofosfolipídios Isolados de Organismos Marinhos da Região de Arraial do Cabo—R J.
8 Berenbaum M. R. (1995). The chemistry of defense: theory and practice. In: Chemical Ecology: the chemistry of biotic interaction, pp 1-16. T. Eisner & J. Meinwald [Editores]. National Academic Press—Washington D.C.
9 Bhadury, P. and Wright, P. C. (2004). Exploitation of marine algae: biogenic compounds for potential antifouling applications. Planta. Vol. 219, pp 561-578.
10 Bhaskar, P. V. and Bhosle, N. B. (2005). Microbial extracellular polymeric substance in marine biogeochemical process. Current Science. Vol. 88, No 1, pp 45-53.
11 Blank M. L.; Snyder F.; Byers L. W. et al.; (1979). Antihypertensive activity of alkyl ether analog of phosphatidylcholine. Biochemical and Biophysical Research Communications. Vol. 90, pp 1194-1200.
12 Bohlin L.; Sjögren M.; Claeson P.; et al. (2004). On-growth inhibiting compounds. Patent WO 2004/055044A1. World Intellectual Property Organization, International Bureau, Geneva, Switzerland.
13 Bonati S, and Monteleone F. (2001). Biocidal-antifouling agents with low ecotoxicity index. Patent WO 01/28328A1. World Intellectual Property Organization, International Bureau, Geneva, Switzerland.
14 Borenstein, S. W. (1994). Microbiologically influenced corrosion handbook. Woodhead publishing Ltd. Cambridge, England. Pp 1-7.
15 Botitsi E.; Mavri-Vavayanni M. and Siafaka-Kapadai A. (1998). Metabolic fate of platelet-activating factor (PAF 1-O-alkyl-2-acetylsn-glycero-3-phosphocholine) and lyso-PAF (1-O-alkyl-2-lysosn-glycero-3-phosphocholine) in FRTL5 cells. Journal of Lipid Research. Vol. 39, pp 1295-1304.
16 Brady R. F. (1999). Properties which influence marine fouling resistance in polymers containing silicon and fluorine. Progress in Organic Coatings. Vol. 35, pp 31-35.
17 Brady R. F. (2000). Clean hulls without poisons: devising and testing nontoxic marine coatings. Journal of Coatings Technology. Vol. 72, pp 45-56.
18 Brady R. F. (2001). A fracture mechanical analysis of fouling release from nontoxic antifouling coatings. Progress in Organic Coatings. Vol. 43, issue 1-3, pp 188-192.
19 Brow, W. J.; Chambers, K. and Doody, A. (2003). Phospholipase A2 (PLA2) enzymes in membrane trafficking: mediators of membrane shape and function. Traffic. Vol. 4, pp 214-221.
20 Butler A. J.; van Altena I. A. and Dunne S. J. (1996). Antifouling activity of lyso-platelet-activating factor extracted from Australian sponge *Crella incrustans*. Journal of Chemical Ecology. Vol. 22, No 11, pp 2041-2061.
21 Callow M. E. (1990). Ship fouling: problems and solutions. Chemistry and Industry. http://www.highbeam.com/library/doc1.asp?ctrlInfo=Round9c%3APr. Accessed on 26 Janeiro 2005.

22 Callow, M. E. and Callow, J. A. (2006). Biofilms. In Progress in molecular and subcellular biology. Subseries Marine Molecular Biotechnology. Fusetani and Clare. Antifouling conpounds. Springer Verlag Berlin 2006, pg 141-169.

23 Christie W. W. (1993). Preparation of lipid extracts from tissues. In Advances in Lipid Methodology, Two, pp 195-213. http://www.lipidlibrary.co.uk. Accessed on 2 Feb. 2005.

24 Clare A. S. (1995). Natural ways to banish barnacles. New Scientist. Vol. 145, pp 38-41.

25 Costerton, J. W.; Lewandowski, Z.; Debeer, D.; et al. (1994). Biofilms the customized microniche. Journal of Bacteriology. Vol. 178, No 8, pp 2137-2142.

26 Croft S. L.; Seifert K.; Duchene M. (2003). Antiprotozoal activities of phospholipids analogues. Molecular & Biochemical Parasitology. Vol. 126, pp 165-172.

27 Davey, M. E. and O'toole, G. A. (2000). Microbial Biofilms: from ecology to molecular genetics. Microbiology and Molecular Biology Reviews. Vol. 64, No 4 pp 847-867.

28 de Beer, D. and Kühl, M. (2001). Interfacial microbial mats and biofilms. In: The Benthic Boundary Layer. Capitulo 15, pp. 374-394. B. P. Boudreau & B. B. Jørgensen (editores.), Oxford University Press, New York.

29 Dekker, N. (2000). Outer-membrane phospholipase A: known structure, unknown biological function. Molecular Microbiology. Vol. 35, No 4, pp 711-717.

30 Dennis, E. A. (1994). Diversity of group types, regulation, and function of phospholipase $A_2$. The Journal of Biological Chemistry. Vol. 269, No 18, pp 13057-13060.

31 Donlan, R. M. (2002). Biofilm: microbial life on surfaces. Emerging Infectious Diseases. Vol. 8, No 9, pp 881-890.

32 Dunne, Jr. W. M. (2002). Bacterial adhesion: seen any good biofilms lately? Clinical Microbiology Reviews. Vol. 15, No 2, pp 155-166.

33 Etoh H.; Kondoh T.; Noda R.; et al. (2002). Shogaols from *Zingiber officinale* as promising antifouling agents. Bioscience Biotechnology Biochemistry. Vol. 66 (8), pp 1748-1750.

34 Etoh H.; Kondoh T.; Yoshioka N.; et al. (2003). 9-Oxoneoprocurcumenol from *Curcuma aromatica* (Zingiberaceae) as an attachment inhibitor against the Blue mussel *Mytilus edulis galloprovincialis*. Bioscience Biotechnology Biochemistry. Vol. 67 (4), pp 911-913.

35 Faulkner D. J. (2000). Marine natural products. Natural Products Report. Vol. 17, pp 7-55

36 Fernandez M. A.; Limaverde A. M.; Castro I. B. (2002). Occurrence of imposex in *Thais haemastoma*: possible evidence of environmental contamination derived from organotin compounds in Rio de Janeiro and Fortaleza, Brazil. Caderno de Saúde Pública. Vol. 18, No 2, pp 463-476.

37 Flemming, H.; Griebe, T. and Schaule, G. (1996). Antifouling strategies in technical systems—a short review. Water Science and Technology. Vol 34, No 5-6, pp 517-524.

38 Foster, M. S; Harrold, C.; Hardin, D. D. (1991). Point vs. photo quadrat estimates of cover of sessile marine organisms. Journal of Experimental Marine Biology and Ecology. Vol. 146, pp. 193-203.

39 Gipperth, L. (2009). The legal design of the international and european union ban on tributyltin antifouling paint: Direct and indirect effects. Journal of Environmental Management. Vol. 90, pp S86-S95.

40 Grunlan M. A.; Lee N. S.; Cai G.; et al. (2004). Synthesis of α ω-Bis epoxy oligo (1'H 1'H 2'H 2'H-perfluoroalkyl siloxane)s and properties of their photo-acid cross-linked films. Chemistry of Materials. Vol. 16, pp 2433-2441.

41 Hayakawa T.; Wang J.; Xiang M.; et al. (2000). Effect of changing molecular end groups on surface properties: synthesis and characterization of poly(styrene-b-semifluorinated isoprene) block copolymers with—CF2H end groups. Macromolecules. Vol. 33, pp 8012-8019.

42 Houve H.; Kleveland K.; Nilsen O. N.; et al. (2001). Novel juvenile hormone analogues and their use as antifouling agents. Patent WO 01/06853 A2. World Intellectual Property Organization, International Bureau, Geneva, Switzerland.

43 IMO—International Maritime Organisation (2010). http://www.imo.org/Newsroom/mainframe.asp?topic_id=1472&doc_id=8473; http://www.imo.org/Newsroom/mainframe.asp?topic_id=1709&doc_id=10131; http://www.imo.org/Newsroom/mainframe.asp?topic_id=67&doc_id=1486. (accessed on 17 Oct. 2010).

44 IUPAC—International Union of Pure and Applied Chemistry (1978). The nomenclature of lipids (Recommnedations 1976). Journal of Lipid Research. Vol. 19, pp 114-128

45 Kohler, K. E.; S. M. Gill. (2006). Coral Point Count with Excel extensions (CPCe): A Visual Basic program for the determination of coral and substrate coverage using random point count methodology. Computers and Geosciences 32 (9), pp 1259-1269

46 Laspidou, C. S. (2003). Modeling Heterogeneous Biofilms Including Active Biomass Inert Biomass and Extracellular Polymeric Substances. Ph.D. Thesis. Northwestern University USA. http://www.scirus.com/srsapp/sciruslink?.

47 Lewis J. A. (2001a). Ship anti-foulants—tributyltin and substitutes. National Shipping Industry Conference, Sydney, Australia, pp 1-6. http://www.amsa.gov.au/about_amsa/Corporate_information/AMSA_speeches/Shipping_In_The_Asia-Pacific_Conference/PDFs/dsto.pdf. Accessed on 10 Jan. 2005.

48 Lewis J. A. (2001b). Hull Fouling as a Vector for the Translocation of Marine Organisms. Report No. 1. Revision 0. Marine Science & Ecology Pty. Ltd. (AMOG Consulting).

49 Lewis J. A. (2002). The Significance of the Prospective Ban on Tributyltin Antifouling Paints on the Introduction & Translocation of Marine Pests in Australia. Report No. 2. Revision 0. Marine Science & Ecology Pty. Ltd. (AMOG Consulting).

50 Lindholm P.; Goransson U.; Johansson S.; et al. (2002). Cyclotides: a novel type of cytotoxic agents. Molecular cancer Therapeutics. Vol. 1, pp 365-369.

51 Loosdrecht, M. C. M. van, Lyklema, J.; Norde, W. and Zehnder, A. J. B. (1990). Influence of interfaces on microbial activity. Microbiological Reviews. Vol. 54, No 1, pp 75-87.

52 Lopes, R. S. C., Lopes, C. C., Batista, W. R., Neves, M. H. C. B., Albert, A. L. M., Cardoso, J. N. (2007). Avaliação da atividade anti-incrustante de glicerofosfolipídios isolados de organismos marinhos da região de Arraial do Cabo-R J, *Revista Pesquisa Naval*, No 19, 140-145.

53 Marathe G. K.; Silva A. R.; Neto H. C. C. F.; et al. (2001). Lysophosphatidylcholine and lyso-PAF display PAF-like activity derived from contaminating phospholipids. Journal of Lipid Research. Vol. 42, pp 1430-1437.

54 Maréchal J. P.; Culioli G.; Hellio C.; et al. (2004). Seasonal variation in antifouling activity of crude extracts of brown alga *Bifurcaria bifurcate* (Cystoseiraceae) against cyprids of *Balunus amphitrite* and marine bacteria *Cobetia marina* and *Pseudoalteromonas halopanktis*. Journal of Experimental Marine Biology and Ecology. Vol. 313, Issue 1, pp 47-62.

55 Matias J. R. (2001). Non-toxic coating composition methods of use thereof and articles protected from attachment of biofouling organisms. Patent Publication No. WO 01/95718A1. World Intellectual Property Organization, International Bureau, Geneva, Switzerland.

56 McIntyre T. M.; Zimmerman G. A. and Prescott S. M. (1999). Biologically active oxidized phospholipids. The Journal of Biological chemistry. Vol. 274, No 36, pp 25189-25192.

57 Mera A. E. and Wynne K. J. (2001). Fluorinated silicone resin fouling release composition. U.S. Pat. No. 6,265,515. United States Patent and Trademark Office.

58 Milne A. (1977). Antifouling marine compositions. U.S. Pat. No. 4,025,693. United States Patent and Trademark Office.

59 Milne A. and Hails G. (1974). Marine paint. Patent GB1457590. UK Patent Office.

60 Nevalainen, T. J.; Quinn, R. J. and Hooper, J. N. A. (2004). Phospholipase A2 in porifera. Comparative Biochemistry and Physiology, Part B. Vol. 137, pp 413-420.

61 Newby B. Z. (2002). Project description: in search of non-toxic antifouling coatings. http://gozips.uakron.edu/~bimin/projectdescription.pdf. Accessed on 10 Jan. 2005.

62 NIWA—National Institute of Water & Atmospheric Research (2002). Protecting our aquatic biodiversity. http://www.niwa.co.nz/pubs/mr/archive/ncabb/abb/2002-01/. Accessed on 14 Jan. 2005.

63 NRC—National Research Council (1996). Stemming the Tide: controlling introduction of nonindigenous species by ships' ballast water. Marine Board Commission on Engineering and Technical Systems. National Academic Press. Washington, D.C.

64 Okino T.; Yoshimura E.; Hirota H. and Fusetani N. (1995). Antifouling kalihinenes from the marine sponge *Acanthella cavernosa*. Tetrahedron Letters. Vol. 36, pp 8637-8640.

65 Paris C.; Loiseau P.M.; Bories C. and Bréard J. (2004). Miltefosine induces apoptosis-like death in *Leishmania donovani* promastigotes. Antimicrobial Agents and Chemotherapy. Vol. 48, No 3, pp 852-859.

66 Parsek, M. R. and Fuqua, C. (2003). Biofilms 2003: emerging themes and challenges in studies of surface-associated microbial life. Journal of Bacteriology. Vol. 186, No 14, pp 4427-4440.

67 Pennings S. C.; Pablo S. R.; Paul V. J. and Duffy E. (1994). Effects of sponge secondary metabolites in different diets on feeding by groups of consumers. Journal of Experimental Marine Biology and Ecology. Vol. 180, pp 137-149.

68 Pereira R. C.; da Gama B. A. P.; Teixeira V. L.; et al. (2003). Ecological roles of natural products of the brazilian red seaweed Laurencia obtuse. Brazilian Journal of Biology. Vol. 63 (4), pp 665-672.

69 Prescott S. M.; Zimmerman G. A. and McIntyre T. M. (1990). Platelet-activating factor. The Journal of Biological Chemistry. Vol. 265, No. 29, pp 17381-17384.

70 PROPELLER magazine. August 2002. International Marine Coatings. www.international-marine.com. Accessed on 10 Jan. 2005.

71 PROPELLER magazine. April 1998. International Marine Coatings. www.international-marine.com. Accessed on 10 Jan. 2005.

72 PROPELLER magazine. March 2004. International Marine Coatings. www.international-marine.com. Accessed on 10 Jan. 2005.

73 PROPELLER magazine. January 2000. International Marine Coatings. www.international-marine.com. Accessed on 10 Jan. 2005.

74 Puglisi M. P.; Paul V. J. and Slattery M. (2000). Biogeographic comparisons of chemical and structural defenses of the Pacific gorgonians *Annella mollis* and *A. reticulata*. Marine Ecological Progress Series. Vol. 207, pp 263-272.

75 Race T. D. and Kelly M. A. (1994). A comparison of metal leachate rate and zebra mussel control efficacy for coatings and materials. www.sgnis.org/publicat/proceed/1994/319.pdf. Accessed on 10 Jan. 2005.

76 Robbart E. (1961). Ship hull coated with antifouling silicone resin and method of coating. U.S. Pat. No. 2,986,474. United State Patent and Trademark Office.

77 Salazar M. H. and Salazar S. M. (1996). Mussels as bioindicators: effects of TBT on survival bioaccumulation and growth under natural conditions. In: Organotin: Environmental Fate and Effects. Chapter 15, pp. 305-330. M. A. Champ and P. F. Seligman (Editor). Editora Chapman & Hall. London, UK.

78 Seifert K.; Duchene M.; Wernsdorfer W. H.; et al. (2001). Effects of miltofosine and other alkylphosphocholines on human intestinal parasite *Entamoeba histolytica*. Antimicrobial Agents and Chemotherapy. Vol. 45, No 5, pp 1505-1510.

79 Stafforini, D. M.; McIntyre, T. M.; Zimmerman, G. A. and Prescott, S. M. (1997). Platelet-activating factor acetylhydrolases. The Journal of Biological Chemistry. Vol. 242, No 29, pp 17895-17898.

80 Stoodley, L. H.; Costerton, J. W. and Stoodley, P. (2004). Bacterial biofilms: from the natural environment to infectious diseases. Nature Reviews. Vol. 2, pp 95-108.

81 Stremler, K. E.; Stafforini, D. M.; Prescott, S. M. et al. (1989). An oxidized derivative of phosphatidylcholine is a substrate for the platelet-activating factor acetylhydrolase from human plasma. The Journal of Biological Chemistry. Vol. 264, No 10, pp 5331-5334.

82 Stupak, M. E.; García, M. T. and Pérez, M. G. (2003). Non-toxic alternative compound for marine antifouling paints. International Biodeterioration & Biodegradetion. Vol. 52, issue 1, pp 4.

83 Susic, M. (2004). Novel quaternary ammonium compounds. Patent Publication No. WO 2004/029017A1. World Intellectual Property Organization, International Bureau, Geneva, Switzerland.

84 Sutherland, I. W. (2001). Biofilm exopolysaccharides: a strong and stick framework. Microbiology. Vol. 147, pp 3-9.

85 Tokumura A.; Takauchi K.; Asai T. et al. (1989). Novel molecular analogues of phosphatidylcholines in a lipid extract from bovine brain: 1-long-chain acyl-2-short-chain acyl-sn-glycero-3-phosphocholines. Journal of Lipid Research. Vol. 30, pp 219-224.

86 Tokumura A.; Sumida T.; Toujima M. et al. (2000). Structural identification of phosphatidylcholines having an oxidatively shortened linoleate residue generated through its oxygenation with soybean or rabbit reticulocyte lipoxygenase. Journal of Lipid Research. Vol. 41, pp 953-962.

87 Tsukamoto S.; Kato H.; Hirota H. and Fusetani N. (1996). Ceratinamides A and B: New antifouling dibromotyrosine derivatives from marine sponge *Pseudoceratina purpurea*. Tetrahedron. Vol. 52, Issue 24, pp 8181-8186.

88 van der Luit A. H.; Budde M.; Ruurs P.; et al. (2002). Alkyl-lysophospholipid accumulates in lipid rafts and induces apoptosis via raft-dependent endocytosis and inhibition of phosphatidylcholine synthesis. The Journal of Biological Chemistry. Vol. 277, No 42, pp 39541-39547.

89 Venable M. E.; Zimmerman G. A.; McIntyre T. M. and Prescott S. M. (1993). Platelet-activating factor: a phospholipid autacoid with diverse actions. Journal of Lipid Research. Vol. 34, pp 691-702.

90 Verma N. K. and Dey C. S. (2004). Possible mechanism of miltofosine-mediated death of *Leishmania* donovani. Antimicrobial Agents and Chemotherapy. Vol. 48, No 8, pp 3010-3015.

91 Watermann B. (1997). Alternative antifouling techniques: present and future. German Journal Hydrograph. Vol. 7, pp 99-108.

92 World Health Organization (1990). Tributyltin Compounds. Environmental Health Criteria. http://www.inchem.org/documents/ehc/ehc/ehc116.htm. Accessed on 10 Jan. 2005.

93 Xiang M.; Li X.; Ober C. K.; et al. (2000). Surface stability in liquid-crystalline block copolymers with semifluorinated monodendron side groups. Macromolecules. Vol. 33, pp 6106-6119.

94 Yebra D. M.; Kiil S, and Dam-Johansen K. (2004). Antifouling technology—past present and future steps towards efficient and environmental friendly antifouling coating. Progress in Organic Coatings. Vol. 50, pp 75-104.

95 Youngblood J. P.; Andruzzi L.; Ober C. K.; et al. (2003). Coatings Based on Side-chain Ether-linked Poly(ethyleneglycol) and Fluorocarbon Polymers for the Control of Marine Biofouling. Biofouling. Vol. 19 (Supplement), pp 91-98.

96 Yulu W.; Pfeffer R. and Dave R. (2004). Polymer coating encapsulation of nanoparticles using a supercritical antisolvent process. Patent Publication No. WO 2004/091571A2. World Intellectual Property Organization, International Bureau, Geneva, Switzerland.

97 Zhou X.; Lu X.; Richard C.; et al. (1996). 1-O-Octadecyl-2-O-methyl-glycerophosphocholine inhibits the transduction of growth signals via the MAPK cascade in cultured mcf-7 cells. Journal of Clinical Investigation. Vol. 98, No 4, pp 937-944.

What is claimed is:

1. A process for the production of a biocidal compound, comprising the step of reacting a compound of formula (II)

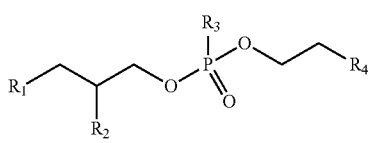

wherein:

R1 is an O-acyl group containing from 18 to 22 carbon atoms, comprising from 0 to 3 unsaturations;

R2 is an O-acyl group containing from 18 to 22 carbon atoms, comprising from 0 to 3 unsaturations;

R3 is OH or O⁻;

R4 is [N⁺(CH$_3$)$_3$] or [N⁺H(CH$_3$)$_2$], with sodium methoxide generated in situ by the reaction of methanol with metallic sodium in a reflux condenser with cold water, coupled with an agitator; and the reaction lasts for about 50-90 hours at a temperature of about 45-60° C.

2. An antifouling composition, comprising:
a) a biocidal compound structure according to formula (I):

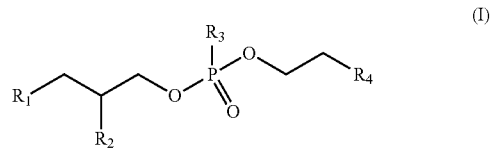

wherein:
i) R1 is OH; R2 is OC(O)C17 with 2 unsaturations; R3 is O—; and R4 is N⁺(CH$_3$)$_3$;
ii) R1 is OH; R2 is OC(O)C17 with 1 unsaturation; R3 is O—; and R4 is N⁺H(CH$_3$)$_2$;
iii) R1 is OH; R2 is OC(O)C17 with 0 unsaturations; R3 is O—; and R4 is N⁺(CH$_3$)$_3$;
iv) R1 is OH; R2 is OC(O)C17 with 3 unsaturations; R3 is O—; and R4 is N⁺(CH$_3$)$_3$;
v) R1 is OH; R2 is OC(O)C17 with 2 unsaturations; R3 is O—; and R4 is N⁺H(CH$_3$)$_2$;
vi) R1 is OH; R2 is OC(O)C17 with 1 unsaturation; R3 is O—; and R4 is N⁺H(CH$_3$)$_2$;
vii) R1 is OH; R2 is OC(O)C17 with 0 unsaturations; R3 is O—; and R4 is N⁺H(CH$_3$)$_2$;
viii) R1 is OH; R2 is OC(O)C17 with 3 unsaturations; R3 is O—; and R4 is CH$_2$N⁺(CH$_3$)$_3$;
ix) R1 is OH; R2 is OC(O)C19 with 2 unsaturations; R3 is O—; and R4 is N⁺H(CH$_3$)$_2$;
x) R1 is OH; R2 is OC(O)C19 with 3 unsaturations; R3 is O—; and R4 is N⁺H(CH$_3$)$_2$; and
xi) combinations thereof;
b) an acceptable vehicle; and
c) copper oxide.

3. A process for the production of an antifouling composition, comprising the step of adding a compound of formula (I) to an existing composition:

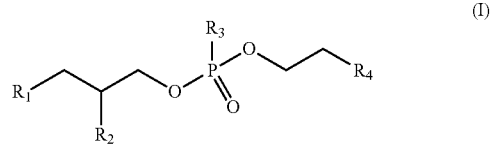

wherein:
i) R1 is OH; R2 is OC(O)C17 with 2 unsaturations; R3 is O—; and R4 is N⁺(CH$_3$)$_3$;
ii) R1 is OH; R2 is OC(O)C17 with 1 unsaturation; R3 is O—; and R4 is N⁺H(CH$_3$)$_2$;
iii) R1 is OH; R2 is OC(O)C17 with 0 unsaturations; R3 is O—; and R4 is N⁺(CH$_3$)$_3$;
iv) R1 is OH; R2 is OC(O)C17 with 3 unsaturations; R3 is O—; and R4 is N⁺(CH$_3$)$_3$;
v) R1 is OH; R2 is OC(O)C17 with 2 unsaturations; R3 is O—; and R4 is N+H(CH$_3$)$_2$;
vi) R1 is OH; R2 is OC(O)C17 with 1 unsaturation; R3 is O—; and R4 is N⁺H(CH$_3$)$_2$;
vii) R1 is OH; R2 is OC(O)C17 with 0 unsaturations; R3 is O—; and R4 is N⁺H(CH$_3$)$_2$;
viii) R1 is OH; R2 is OC(O)C17 with 3 unsaturations; R3 is O—; and R4 is CH$_2$N⁺(CH$_3$)$_3$;
ix) R1 is OH; R2 is OC(O)C19 with 2 unsaturations; R3 is O—; and R4 is N⁺H(CH$_3$)$_2$;

x) R1 is OH; R2 is OC(O)C19 with 3 unsaturations; R3 is
O—; and R4 is $N^+H(CH_3)_2$; and
xi) combinations thereof.

4. A method to prevent fouling, comprising the step of applying an antifouling composition on a suitable surface before placing the surface in contact with water, the antifouling composition comprising:
   a) a biocidal compound structure according to formula (I):

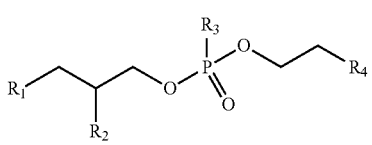

wherein:
   R1 is a hydroxyl group or an O-acyl group containing from 2 to 22 carbon atoms, comprising from 0 to 3 unsaturations;
   R2 is a hydroxyl group or an O-acyl group containing from 2 to 22 carbon atoms, comprising from 0 to 3 unsaturations;
   R3 is OH or O⁻; and
   R4 is $[N^+(CH_3)_3]$ or $[N^+H(CH_3)_2]$, and
   b) an acceptable vehicle.

5. The method according to claim 4, wherein the surface is selected from the group consisting of hulls of ships, vessels, yachts, sailboats, rafts, submarines, ferries, speedboats, frigates, aircraft carriers, icebreakers, rowboat, sloop, tug vessels, planks surfing, windsurfing, water skiing, buoys, piers, breakwaters, oil platforms, fences, farming, fishing nets, underwater cages, oxygen tanks and diving equipment, periscopes, rudders, propellers, keels, surfaces of equipment connected the water treatment, desalination, hydroelectric plants, and food processing, membranes, filters, piping, valves, pumps, condensers, evaporators, heat exchangers, and combinations thereof.

6. The method according to claim 4, wherein the compound a) is selected from the group consisting of:
   i) R1 is OH; R2 is OC(O)C17 with 2 unsaturations; R3 is O—; and R4 is $N^+(CH_3)_3$;
   ii) R1 is OH; R2 is OC(O)C17 with 1 unsaturation; R3 is O—; and R4 is $N^+H(CH_3)_2$;
   iii) R1 is OH; R2 is OC(O)C17 with 0 unsaturations; R3 is O—; and R4 is $N^+(CH_3)_3$;
   iv) R1 is OH; R2 is OC(O)C17 with 3 unsaturations; R3 is O—; and R4 is $N^+(CH_3)_3$;
   v) R1 is OH; R2 is OC(O)C17 with 2 unsaturations; R3 is O—; and R4 is $N^+H(CH_3)_2$;
   vi) R1 is OH; R2 is OC(O)C17 with 1 unsaturation; R3 is O—; and R4 is $N^+H(CH_3)_2$;
   vii) R1 is OH; R2 is OC(O)C17 with 0 unsaturations; R3 is O—; and R4 is $N^+H(CH_3)_2$;
   viii) R1 is OH; R2 is OC(O)C17 with 3 unsaturations; R3 is O—; and R4 is $CH_2N^+(CH_3)_3$;
   ix) R1 is OH; R2 is OC(O)C19 with 2 unsaturations; R3 is O—; and R4 is $N^+H(CH_3)_2$;
   x) R1 is OH; R2 is OC(O)C19 with 3 unsaturations; R3 is O—; and R4 is $N^+H(CH_3)_2$; and
   xi) combinations thereof.

7. The method according to claim 4, further comprising an additional antifouling active selected from the group consisting of antifungal agents, algaecides, pesticides, and combinations thereof.

8. The method according to claim 7, wherein the additional antifouling active is copper oxide.

9. The method according to claim 4, wherein the vehicle comprises at least two components selected from the group consisting of:
   a) binders selected from the group consisting of polyvinyl chloride, acrylic resins, copolymer of vinyl chloride, vinyl acetate, rubber of acrylonitrile-butadiene-stireno, in one of a solvent system, an aqueous dispersion, and a combined solvent system and aqueous dispersion;
   b) organic pigments, inorganic pigments, insoluble dyes;
   c) plasticizers; and
   d) viscosity modifiers.

10. A method to turn a surface into an antifouling surface, comprising the step of applying an antifouling composition to an appropriate area of the surface, the antifouling composition comprising:
   a) a biocidal compound structure according to formula (I):

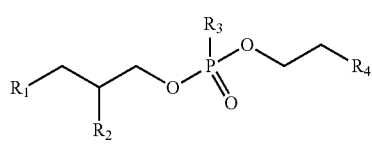

wherein:
   i) R1 is OH; R2 is OC(O)C17 with 2 unsaturations; R3 is O—; and R4 is $N^+(CH_3)_3$;
   ii) R1 is OH; R2 is OC(O)C17 with 1 unsaturation; R3 is O—; and R4 is $N^+H(CH_3)_2$;
   iii) R1 is OH; R2 is OC(O)C17 with 0 unsaturations; R3 is O—; and R4 is $N^+(CH_3)_3$;
   iv) R1 is OH; R2 is OC(O)C17 with 3 unsaturations; R3 is O—; and R4 is $N^+(CH_3)_3$;
   v) R1 is OH; R2 is OC(O)C17 with 2 unsaturations; R3 is O—; and R4 is $N^+H(CH_3)_2$;
   vi) R1 is OH; R2 is OC(O)C17 with 1 unsaturation; R3 is O—; and R4 is $N^+H(CH_3)_2$;
   vii) R1 is OH; R2 is OC(O)C17 with 0 unsaturations; R3 is O—; and R4 is $N+H(CH_3)_2$;
   viii) R1 is OH; R2 is OC(O)C17 with 3 unsaturations; R3 is O—; and R4 is $CH_2N^+(CH_3)_3$;
   ix) R1 is OH; R2 is OC(O)C19 with 2 unsaturations; R3 is O—; and R4 is $N^+H(CH_3)_2$;
   x) R1 is OH; R2 is OC(O)C19 with 3 unsaturations; R3 is O—; and R4 is $N^+H(CH_3)_2$; and
   xi) combinations thereof; and
   b) an acceptable vehicle.

11. The method according to claim 10, wherein the surface is selected from the group consisting of hulls of ships, vessels, yachts, sailboats, rafts, submarines, ferries, speedboats, frigates, aircraft carriers, icebreakers, rowboat, sloop, tug vessels, planks surfing, windsurfing, water skiing, buoys, piers, breakwaters, oil platforms, fences, farming, fishing nets, underwater cages, oxygen tanks and diving equipment, periscopes, rudders, propellers, keels, surfaces of equipment connected the water treatment, desalination, hydroelectric plants, and food processing, membranes, filters, piping, valves, pumps, condensers, evaporators, heat exchangers, and combinations thereof.

12. The method according to claim 10, further comprising copper oxide as an additional antifouling active.

13. The method according to claim 10, wherein the vehicle comprises:

a) binders selected from the group consisting of polyvinyl chloride, acrylic resins, copolymer of vinyl chloride, vinyl acetate, rubber of acrylonitrile-butadiene-styrene, in one of a solvent system, an aqueous dispersion, and a combined solvent system and aqueous dispersion;
b) organic pigments, inorganic pigments, insoluble dyes;
c) plasticizers;
d) viscosity modifiers; and
e) combinations thereof.

14. A biocidal method comprising the steps of:
a) incorporating a compound having a structure according to formula (I):

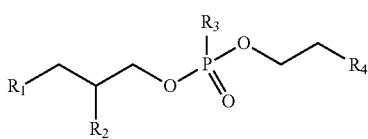

(I)

wherein:
R1 is a hydroxyl group;
R2 is an O-acyl group containing from 17 to 20 carbon atoms and comprising from 0 to 3 unsaturations;
R3 is OH or O$^-$; and
R4 is [N$^+$(CH$_3$)$_3$] or [N$^+$H(CH$_3$)$_2$],
into a base paint; and
b) contacting the base paint obtained in a) with a surface.

15. The biocidal method according to claim 14, wherein the surface is selected from the group consisting of hulls of ships, vessels, yachts, sailboats, rafts, submarines, ferries, speedboats, frigates, aircraft carriers, icebreakers, rowboat, sloop, tug vessels, planks surfing, windsurfing, water skiing, buoys, piers, breakwaters, oil platforms, fences, farming, fishing nets, underwater cages, oxygen tanks and diving equipment, periscopes, rudders, propellers, keels, surfaces of equipment connected the water treatment, desalination, hydroelectric plants, and food processing, membranes, filters, piping, valves, pumps, condensers, evaporators, heat exchangers, and combinations thereof.

16. The biocidal method according to claim 14 wherein the compound of step a) is selected from the group consisting of:
i) R1 is OH; R2 is OC(O)C17 with 0 unsaturations; R3 is O—; and R4 is N$^+$(CH$_3$)$_3$or N$^+$H(CH$_3$)$_2$;
ii) R1 is OH; R2 is OC(O)C17 with 1 unsaturation; R3 is O—; and R4 is N$^+$(CH$_3$)$_3$or N$^+$H(CH$_3$)$_2$;
iii) R1 is OH; R2 is OC(O)C17 with 2 unsaturations; R3 is O—; and R4 is N$^+$(CH$_3$)$_3$or N$^+$H(CH$_3$)$_2$;
iv) R1 is OH; R2 is OC(O)C17 with 3 unsaturations; R3 is O—; and R4 is N$^+$(CH$_3$)$_3$or N$^+$H(CH$_3$)$_2$;
v) R1 is OH; R2 is OC(O)C19 with 2 unsaturations; R3 is O—; and R4 is N$^+$(CH$_3$)$_3$or N$^+$H(CH$_3$)$_2$; and
vi) R1 is OH; R2 is OC(O)C19 with 3 unsaturations; R3 is O—; and R4 is N$^+$(CH$_3$)$_3$or N$^+$H(CH$_3$)$_2$.

* * * * *